United States Patent
Yeung et al.

(12) 
(10) Patent No.: US 10,765,304 B2
(45) Date of Patent: Sep. 8, 2020

(54) ENDOSCOPIC SYSTEMS, DEVICES, AND METHODS FOR PERFORMING IN VIVO PROCEDURES

(71) Applicant: Bio-Medical Engineering (HK) Limited, Hong Kong (CN)

(72) Inventors: Chung-Kwong Yeung, Hong Kong (CN); Wai-Lun Law, Hong Kong (CN); Ka-Wai Kwok, Hong Kong (CN)

(73) Assignee: Bio-Medical Engineering (HK) Limited, Hong Kong (CN)

( * ) Notice: Subject to any disclaimer, the term of this patent is extended or adjusted under 35 U.S.C. 154(b) by 145 days.

(21) Appl. No.: 14/985,587

(22) Filed: Dec. 31, 2015

(65) Prior Publication Data

US 2017/0086658 A1 Mar. 30, 2017

Related U.S. Application Data

(60) Provisional application No. 62/233,828, filed on Sep. 28, 2015.

(51) Int. Cl.
*A61B 1/00* (2006.01)
*A61B 17/02* (2006.01)
(Continued)

(52) U.S. Cl.
CPC .......... *A61B 1/00154* (2013.01); *A61B 1/008* (2013.01); *A61B 1/00082* (2013.01);
(Continued)

(58) Field of Classification Search
CPC ... A61B 1/00082; A61B 1/31; A61B 1/00071; A61B 1/00094; A61B 1/00131;
(Continued)

(56) References Cited

U.S. PATENT DOCUMENTS 4,176,662 A 12/1979 Frazer
5,398,670 A 3/1995 Ortiz et al.
(Continued)

FOREIGN PATENT DOCUMENTS

CN 1051125 A 5/1991
CN 1636499 A 7/2005
(Continued)

OTHER PUBLICATIONS

First Office Action with Search Report issued by PRC State Intellectual Property Office in related PRC Application No. CN 201610147810.9, dated Jan. 4, 2017.
(Continued)

*Primary Examiner* — Ryan N Henderson
(74) *Attorney, Agent, or Firm* — Baker & McKenzie LLP

(57) ABSTRACT

Example embodiments relate to devices, systems, and methods for performing a diagnostic and/or therapeutic action. The system may comprise an elongated main body having a first end. The system may further comprise an anchor assembly attached to the main body near the first end of the main body. The anchor assembly may comprise a first expandable member. The first expandable member may be configurable to expand radially away from the main body. The anchor assembly may further comprise a second expandable member provided between the first expandable member and the first end of the main body. The second expandable member may be configurable to expand radially away from the main body. The anchor assembly may be operable to secure the main body with respect to an interior wall forming the cavity of the patient.

32 Claims, 17 Drawing Sheets

(51) Int. Cl.

| | |
|---|---|
| A61B 10/04 | (2006.01) |
| A61B 1/31 | (2006.01) |
| A61M 25/10 | (2013.01) |
| A61B 1/008 | (2006.01) |
| A61B 1/015 | (2006.01) |
| A61B 1/045 | (2006.01) |
| A61B 17/00 | (2006.01) |
| A61B 17/30 | (2006.01) |
| A61B 17/22 | (2006.01) |

(52) U.S. Cl.
CPC ...... *A61B 1/00094* (2013.01); *A61B 1/00135* (2013.01); *A61B 1/00147* (2013.01); *A61B 1/015* (2013.01); *A61B 1/045* (2013.01); *A61B 1/31* (2013.01); *A61B 10/04* (2013.01); *A61B 17/0218* (2013.01); *A61M 25/1002* (2013.01); *A61B 2017/00269* (2013.01); *A61B 2017/00296* (2013.01); *A61B 2017/00557* (2013.01); *A61B 2017/22069* (2013.01); *A61B 2017/306* (2013.01); *A61M 2025/1015* (2013.01); *A61M 2025/1047* (2013.01); *A61M 2025/1052* (2013.01); *A61M 2025/1086* (2013.01)

(58) Field of Classification Search
CPC ............ A61B 1/00135; A61B 1/00142; A61B 1/00147; A61B 1/00154; A61B 1/00156; A61B 1/005; A61B 1/0051; A61B 1/0057; A61B 1/008; A61B 1/01; A61M 25/1011; A61M 25/1009; A61M 25/1006
USPC ................................. 600/114–116, 121–125; 604/95.01–95.05, 101.01–101.05, 604/102.01–102.03
See application file for complete search history.

(56) References Cited

U.S. PATENT DOCUMENTS

| | | | | |
|---|---|---|---|---|
| 5,619,993 | A | 4/1997 | Lee | |
| 6,007,482 | A | 12/1999 | Madni et al. | |
| 7,935,047 | B2 | 5/2011 | Yoshida et al. | |
| 2001/0007917 | A1 | 7/2001 | Hayakawa et al. | |
| 2004/0186349 | A1* | 9/2004 | Ewers ................ | A61B 1/00082 600/114 |
| 2005/0137457 | A1 | 6/2005 | Machida | |
| 2007/0015965 | A1 | 1/2007 | Cox et al. | |
| 2007/0244361 | A1 | 10/2007 | Ikeda et al. | |
| 2007/0249906 | A1 | 10/2007 | Gorini et al. | |
| 2008/0091068 | A1 | 4/2008 | Terliuc | |
| 2008/0249356 | A1* | 10/2008 | Motai ................ | A61B 1/00154 600/114 |
| 2009/0062611 | A1* | 3/2009 | Toyama ............. | A61B 1/00082 600/118 |
| 2009/0118582 | A1* | 5/2009 | Tsumaru ............ | A61B 1/00156 600/114 |
| 2009/0227835 | A1 | 9/2009 | Terliuc | |
| 2011/0190583 | A1* | 8/2011 | Ashida ...................... | A61B 1/00 600/115 |
| 2012/0077920 | A1 | 3/2012 | Hirano et al. | |
| 2013/0261544 | A1* | 10/2013 | Hardin ............... | A61M 25/1011 604/101.05 |
| 2014/0086772 | A1 | 3/2014 | Olsen | |
| 2014/0318118 | A1 | 10/2014 | Mazzeo et al. | |
| 2015/0070904 | A1 | 3/2015 | Martinez et al. | |
| 2015/0283699 | A1 | 10/2015 | Morin et al. | |
| 2017/0086658 | A1 | 3/2017 | Yeung et al. | |

FOREIGN PATENT DOCUMENTS

| | | |
|---|---|---|
| CN | 1933765 A | 3/2007 |
| CN | 101313839 A | 12/2008 |
| CN | 101378691 A | 3/2009 |
| CN | 201222163 Y | 4/2009 |
| CN | 101632572 A | 1/2010 |
| CN | 102178504 A | 9/2011 |
| CN | 103142199 A | 6/2013 |
| CN | 103462583 A | 12/2013 |
| CN | 204182562 U | 3/2015 |
| CN | 204192562 U | 3/2015 |
| CN | 204379366 U | 6/2015 |
| CN | 105816242 A | 8/2016 |
| CN | 105832279 A | 8/2018 |
| CN | 105832279 A | 8/2019 |
| JP | H0563551 U | 8/1993 |
| JP | H0889476 | 4/1996 |
| JP | 2008237812 A | 10/2008 |
| WO | 2016/051952 A1 | 4/2016 |
| WO | 2017054372 A1 | 4/2017 |

OTHER PUBLICATIONS

Endotics: Painless and Safer Colonscope, http://www.endotics.com, downloaded Mar. 15, 2016, 6 pages.
Giview: Colonoscopy Solution: Safe and Easy-to-Use Colonoscopy, http://www.giview.com, downloaded Mar. 15, 2016, 17 pages.
Third Eye Panoramic: Avantis Medical Systems, http://www.thirdeyepanoramic.com, downloaded Mar. 15, 2016, 15 pages.
Dogangil, G., et al., "A review of medical robotics for minimally invasive soft tissue surgery," Proceedings of the Institution of Mechanical Engineers, Part H: Journal of Engineering in Medicine, vol. 224, (2010), pp. 653-679.
Tumino, E., et al., "Endotics system vs colonoscopy for the detection of polyps," WJG: World Journal of Gastroenterology, (Nov. 21, 2010), vol. 16, No. 43, pp. 5452-5456.
Elsayed, Y., et al., "Finite Element Analysis and Design Optimization of a Pneumatically Actuating Silicone Module for Robotic Surgery Applications," Soft Robotics, vol. 2, No. 00, (2014), pp. 255-262.
Patel, N., et al., "Flexible platforms for natural orifice transluminal and endoluminal surgery," Endoscopy International Open, (2014), vol. 02, pp. E117-E123.
Patel, N., et al., "The endoscopy evolution: 'the superscope era'," Frontline Gastroenterology, (2014), Published online May 13, 2014, http://fg.bmj.com, vol. 0, pp. 1-7.
International Search Report and Written Opinion, PCT/CN2016/070906, dated Jun. 22, 2016, 13 pages.
International Search Report of PCT/CN2017/102964 dated Dec. 25, 2017, 5 pgs.
Written Opinion of PCT/CN2017/102964 dated Dec. 25, 2017, 4 pgs.
First Office Action dated Jan. 19, 2020 in connection with Chinese Application No. 20180557091.7, 8 pages.
Extended European Search Report dated Dec. 2, 2019 in connection with European Application No. 18759231.6, 7 pages.
Extended European Search Report dated Nov. 6, 2019 in connection with European Application No. 17875377.8, 7 pages.
Second Office Action dated Jul. 22, 2019 in connection with Chinese Application No. 20170993140.7, 15 pages.
Office Action dated Apr. 15, 2020 in connection with Chinese Application No. 201810955134.7, 18 pages.
Office Action dated May 21, 2020 in connection with Indian Application No. 2018170376, 5 pages.
Examination Report dated Jun. 15, 2020 in connection with Indian Application No. 201817037440, 7 pages.

* cited by examiner

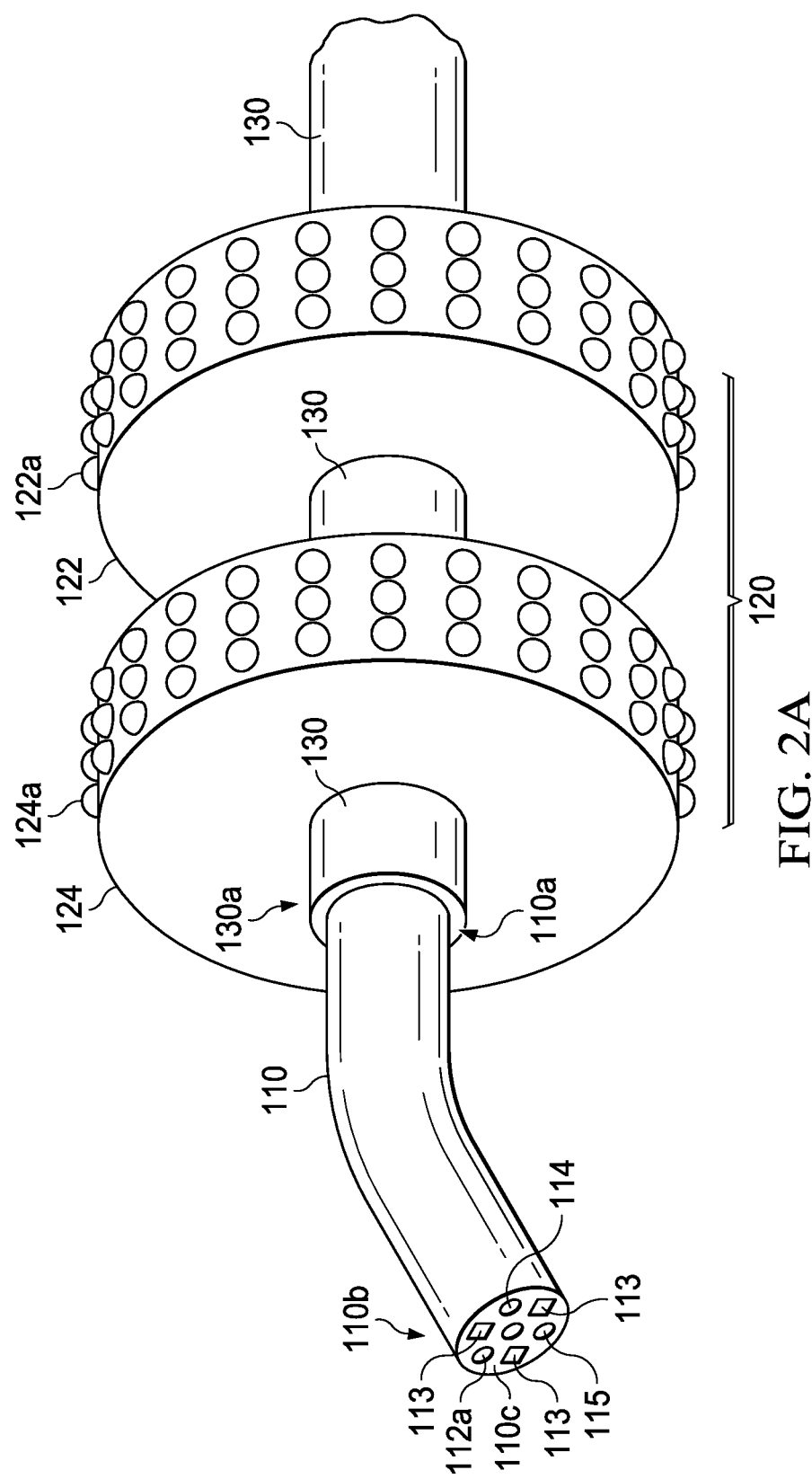

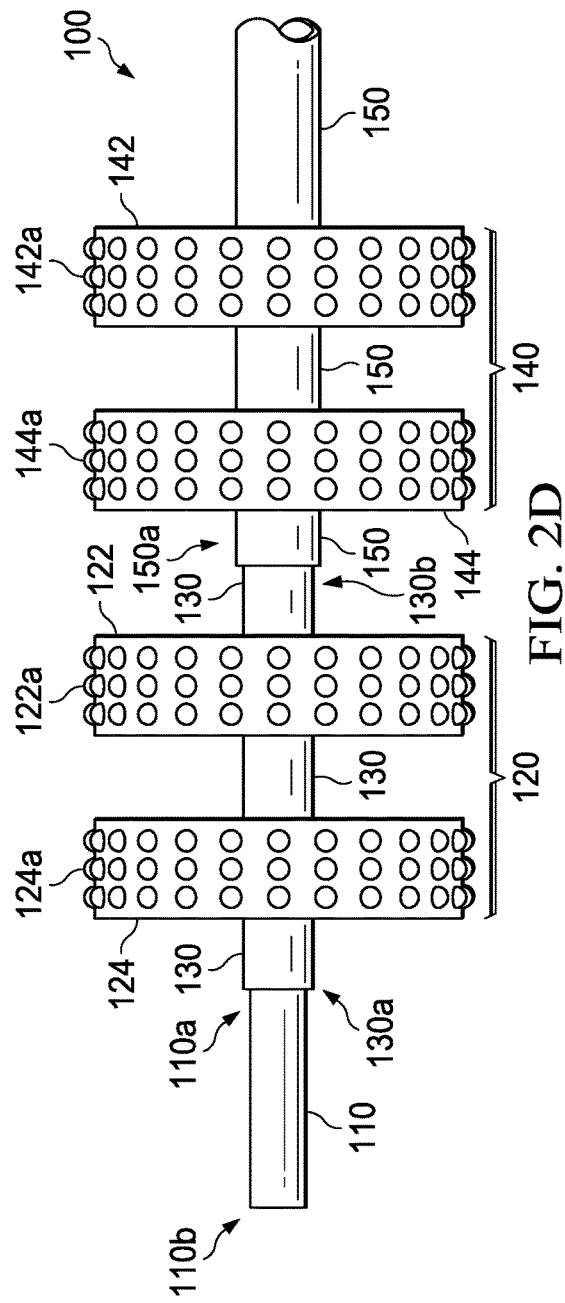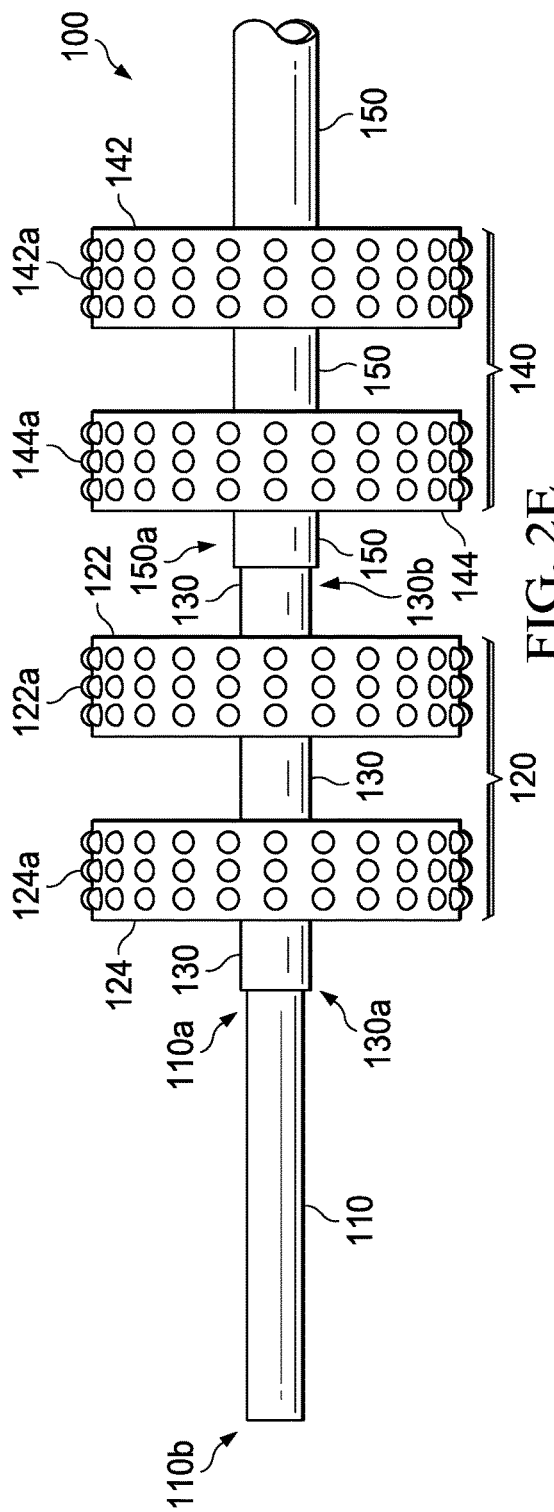
FIG. 2D
FIG. 2E

ENDOSCOPIC SYSTEMS, DEVICES, AND METHODS FOR PERFORMING IN VIVO PROCEDURES

This application claims the benefit of and priority to U.S. Provisional Application No. 62/233,828, filed on Sep. 28, 2015, which application is incorporated herein by reference in its entirety.

BACKGROUND

The present disclosure relates generally to endoscopic systems, devices, and methods, and more specifically, relates to systems and devices for use in performing endoluminal procedures, including diagnostic and therapeutic procedures, and methods of configuring and using such systems and devices.

Presently, colorectal cancer is the third most commonly diagnosed cancer and also the third leading cause of cancer-related deaths worldwide. If diagnosed at a sufficiently early stage, however, the survival rate of patients suffering from colorectal cancer may reach upwards of ninety percent.

Conventional optical colonoscopy is the most widely accepted and used procedure for colorectal screening. In general, conventional optical colonoscopy involves the insertion of a colonoscope through the colon of a patient, and requires forceful manual pushing of the colonoscope against the luminal wall at flexural or looping/bending sections of the colon during insertion, which generally results in severe discomfort and pain to the patient. The retracting and/or removal of the colonoscope from the flexural and/or looping/bending sections of the colon of the patient may also cause significant discomfort and/or pain to the patient.

BRIEF SUMMARY

Despite recent developments in modern medical science and technology, it is recognized in the present disclosure that one or more problems are encountered in colonoscopy-related diagnostic and therapeutic technologies and methodologies, including those described above and in the present disclosure.

Present example embodiments relate generally to systems, devices, and methods for addressing one or more problems in diagnostic and therapeutic systems, devices, and methods, including those described above and herein.

In an exemplary embodiment, an endoscopic system is described. The endoscopic system is configurable to be provided in a cavity of a patient. The endoscopic system may comprise a main body. The main body may be an elongated body having a first end. The endoscopic system may further comprise an anchor assembly attached to the main body near the first end of the main body. The anchor assembly may comprise a first expandable member. The first expandable member may be configurable to expand radially away from the main body. The anchor assembly may further comprise a second expandable member provided between the first expandable member and the first end of the main body. The second expandable member may be configurable to expand radially away from the main body. The anchor assembly may be operable to secure the main body with respect to an interior wall forming the cavity of the patient by expanding the first expandable member to contact the interior wall forming the cavity of the patient and expanding the second expandable member to contact the interior wall forming the cavity of the patient.

In another exemplary embodiment, an endoscopic system is described. The endoscopic system is configurable to be provided in a cavity of a patient. The endoscopic system may comprise a main body. The main body may be an elongated body having a first end. The endoscopic system may further comprise a head assembly. The head assembly may have a first end portion and a second end portion opposite to the first end portion. The first end portion may be attachable to the first end of the main body. The second end portion may be selectively configurable to actuate in a plurality of directions with respect to the first end portion. The head assembly may further comprise an image capturing assembly provided in the second end portion. The image capturing assembly may be configurable to capture an image. The head assembly may further comprise an instrument section provided in the second end portion. The instrument section may be configurable to provide an instrument. The instrument may comprise at least two degrees of freedom of movement for performing an in vivo procedure in the cavity of the patient.

In another exemplary embodiment, a method is described. The method may be for use in configuring an endoscopic system to perform a diagnostic and/or therapeutic/surgical action and/or procedure in a cavity, such as a colonic lumen, of a patient. The method may comprise providing an endoscopic system. The endoscopic system may comprise a first main body. The first main body may be an elongated body having a first end. The endoscopic system may further comprise a second main body. The second main body may comprise a first end and a main cavity. The main cavity may house at least a portion of the first main body. The first main body and second main body may be slidable with respect to each other. The endoscopic system may further comprise an anchor assembly attached to the first main body near the first end of the first main body. The anchor assembly may comprise a first expandable member. The first expandable member may be configurable to expand radially away from the first main body. The anchor assembly may further comprise a second expandable member provided between the first expandable member and the first end of the first main body. The second expandable member may be configurable to expand radially away from the first main body. The endoscopic system may further comprise a second anchor assembly attached to the second main body near the first end of the second main body. The second anchor assembly may comprise a third expandable member. The third expandable member may be configurable to expand radially away from the second main body. The second anchor assembly may further comprise a fourth expandable member provided between the third expandable member and the first end of the second main body. The fourth expandable member may be configurable to expand radially away from the second main body. The endoscopic system may further comprise a head assembly. The head assembly may comprise a first end portion and a second end portion opposite to the first end portion. The first end portion may be attachable to the first end of the first main body. The second end portion may be selectively configurable to actuate in a plurality of directions with respect to the first end portion. The head assembly may further comprise an image capturing assembly provided in the second end portion. The image capturing assembly may be configurable to capture an image. The head assembly may further comprise an instrument section provided in the second end portion. The instrument section may be configurable to provide an instrument. The instrument may have at least two degrees of freedom of movement for performing an endoluminal procedure in patients. The method may further comprise advancing the head assembly through the cavity of the patient. The first end portion of the head assembly may be fixedly attached to the first end of the first main body, and at least a portion of the first main body may be housed in the main cavity of the second main body. The method may further comprise identifying, via an image captured by the image capturing assembly, a direction of the cavity of the patient. The method may further comprise advancing the head assembly along the identified direction of the cavity of the patient by actuating the direction of the second end portion of the head assembly based on the identified direction of the cavity of the patient.

BRIEF DESCRIPTION OF THE DRAWINGS

For a more complete understanding of the present disclosure, example embodiments, and their advantages, reference is now made to the following description taken in conjunction with the accompanying drawings, in which like reference numbers indicate like features, and:

FIG. 2A is an illustration of a perspective view of an example embodiment of the head assembly;

FIG. 2D is an illustration of a side view of an example embodiment of the endoscopic system;

FIG. 2E is an illustration of a side view of an example embodiment of the endoscopic system having the head assembly controlled to extend outwardly, as compared to the head assembly of FIG. 2D;

Although similar reference numbers may be used to refer to similar elements in the figures for convenience, it can be appreciated that each of the various example embodiments may be considered to be distinct variations.

Figure 1:
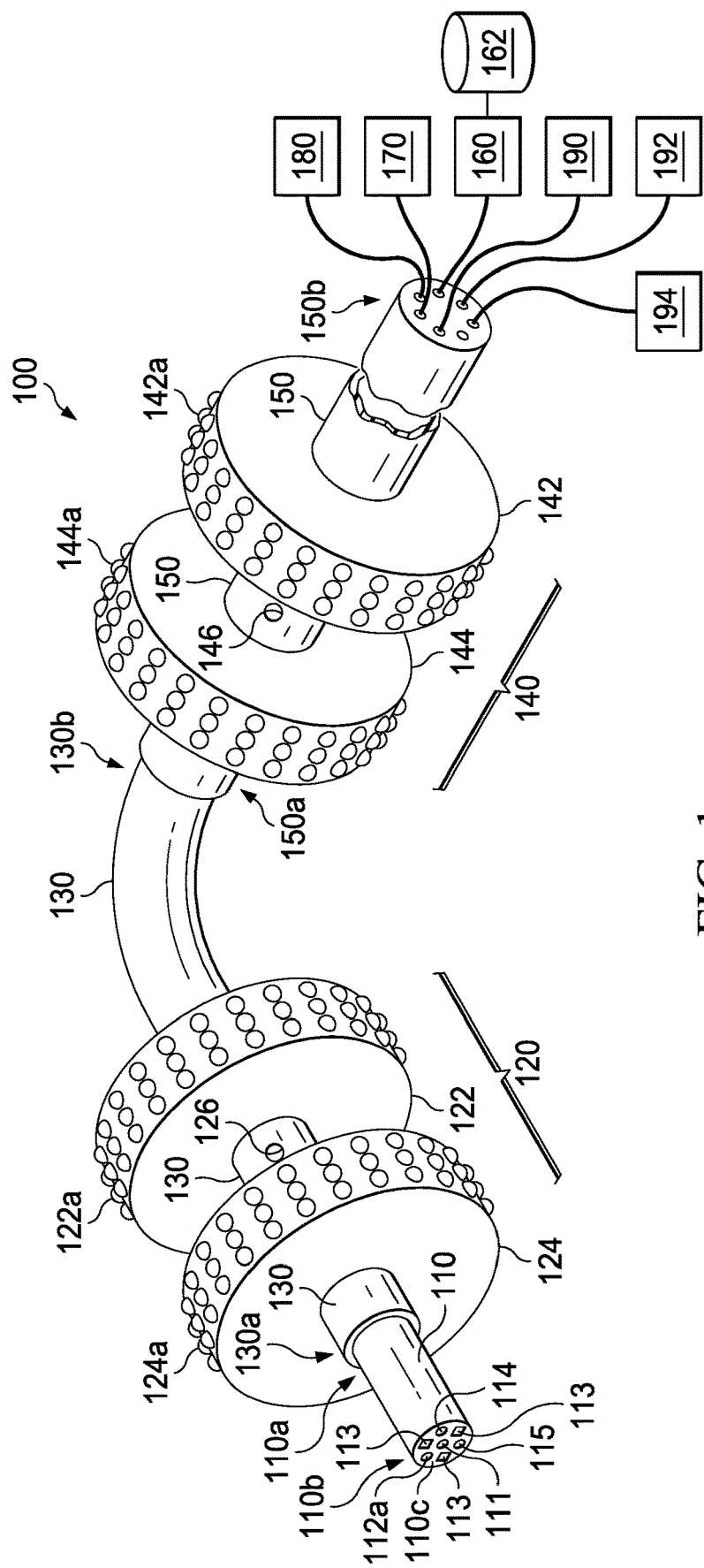
FIG. 1 is an illustration of a perspective view of an example embodiment of an endoscopic system.

Example embodiments will now be described with reference to the accompanying drawings, which form a part of the present disclosure, and which illustrate example embodiments which may be practiced. As used in the present disclosure and the appended claims, the terms "example embodiment," "exemplary embodiment," and "present embodiment" do not necessarily refer to a single embodiment, although they may, and various example embodiments may be readily combined and/or interchanged without departing from the scope or spirit of example embodiments. Furthermore, the terminology as used in the present disclosure and the appended claims is for the purpose of describing example embodiments only and is not intended to be limitations. In this respect, as used in the present disclosure and the appended claims, the term "in" may include "in" and "on," and the terms "a," "an" and "the" may include singular and plural references. Furthermore, as used in the present disclosure and the appended claims, the term "by" may also mean "from," depending on the context. Furthermore, as used in the present disclosure and the appended claims, the term "if" may also mean "when" or "upon," depending on the context. Furthermore, as used in the present disclosure and the appended claims, the words "and/or" may refer to and encompass any and all possible combinations of one or more of the associated listed items.

DETAILED DESCRIPTION

It is recognized in the present disclosure that one or more problems are encountered in colonoscopy-related diagnostic and therapeutic technologies and methodologies, including those described above and in the present disclosure. For example, conventional optical colonoscopy generally involves an insertion of a colonoscope through a colon of a patient, and requires forceful manual pushing of the colonoscope against the interior luminal walls forming the colon cavity at flexural or looping/bending sections of the colon during insertion, which generally results in severe discomfort and/or pain to the patient. Furthermore, the retracting and/or removal of the colonoscope, including the traversing of the colonoscope through the flexural and/or looping/bending sections of the colon of the patient, may also give rise to discomfort and/or pain to the patient.

Recent developments in diagnostic procedures and devices have attempted to address the aforementioned problem through the use of a miniaturized wireless capsule having an integrated camera. To perform the diagnostic procedure, the miniaturized capsule is orally introduced into a patient, and the miniaturized capsule passively navigates via peristalsis along the gastrointestinal tract in a painless manner. It is recognized in the present disclosure, however, that while such recent developments address the issue of discomfort and pain to patients, such recent developments are not without its own problems and limitations. For example, the in vivo monitoring of the gastrointestinal tract by such miniaturized capsules is in fact performed in a non-controlled and very slow manner since locomotion of the miniaturized capsule through the gastrointestinal tract occurs via peristalsis. Furthermore, while a miniaturized capsule generally takes between about 20 to 36 hours to travel through an entire gastrointestinal tract, current power capacity and consumption of such miniaturized capsules are only capable of roughly about eight hours of operation. Accordingly, not all of the gastrointestinal tract can be imaged and/or monitored using such technology. Furthermore, such miniaturized capsules are merely capable of performing imaging/diagnosing procedures, and not capable of performing therapeutic/surgical procedures, such as a removing of polyps, obtaining biopsy samples, and/or the like.

Systems, devices, and methods, including those for use in endoscopy and colonoscopy, are described in the present disclosure for addressing one or more problems of known systems, devices, and methods, including those described above and in the present disclosure. It is to be understood that the principles described in the present disclosure may be applied outside of the context of endoscopy and colonoscopy, such as performing diagnostic procedures, surgical or therapeutic procedures, scientific experiments, and/or other procedures in the same and/or other environments, cavities, and/or organs not described in the present disclosure without departing from the teachings of the present disclosure.

The Endoscopic System (e.g., Endoscopic System 100)

FIG. 1 illustrates a perspective view of an example embodiment of an endoscopic system 100. The endoscopic system 100 may comprise a head assembly 110. The endoscopic system 100 may further comprise a main body 130. The main body 130 may be attachable to the head assembly 110. For example, a first end 130a of the main body 130 may be fixedly attached to a first end portion 110a of the head assembly 110. The endoscopic system 100 may further comprise an anchor assembly 120. The anchor assembly 120 may be attachable to the main body 130. For example, the anchor assembly 120 may be fixedly attached to the main body 130 near the first end 130a of the main body 130. The endoscopic system 100 may further comprise a second main body 150. The second main body 150 may house at least a portion of the main body 130, and the main body 130 and the second main body 150 may be slidable with respect to one another. In this regard, the second main body 150 may comprise a main cavity, and the main cavity may perform the said housing of the main body 130. The endoscopic system 100 may further comprise a second anchor assembly 140. The second anchor assembly 140 may be attachable to the second main body 150. For example, the second anchor assembly 140 may be fixedly attached to the second main body 150 near the first end 150a of the second main body 150. The endoscopic system 100 may further comprise a controller 160. These and other elements of the endoscopic system 100 will now be described with reference to FIGS. 1 to 5.

The Head Assembly (e.g., Head Assembly 110)

FIG. 1 and FIGS. 2A-C illustrate an example embodiment of the head assembly 110 of the endoscopic system 100. The head assembly 110 may comprise first end portion 110a and second end portion 110b opposite to the first end portion 110a. The first end portion 110a of the head assembly 110 may be attachable to the first end 130a of the main body 130 in example embodiments. During diagnostic and/or therapeutic/surgical procedures, the first end portion 110a may be fixedly attached to the first end 130a of the main body 130, as illustrated in at least FIGS. 1 to 3. It is to be understood in the present disclosure that example embodiments of the endoscopic system 100 may comprise one or more other head assemblies, such as head assembly 110' illustrated in FIG. 2B, fixedly attached to one or more other portions of the endoscopic system 100 in addition to or in replacement of the head system 110 attached to the first end 130a of the main body 130.

The head assembly 110 may comprise one or more image capturing assemblies 111, as illustrated in at least FIGS. 1 and 2A. Each image capturing assembly 111 may be any image capturing device, such as a digital and/or analog camera, digital and/or analog video camera, three dimensional (3-D) digital and/or analog camera, 3-D digital and/or analog video camera, holographic camera, x-ray based device, infrared-based device, and/or the like. Each image capturing assembly 111 may comprise one or more lenses, or the like, and may be configurable to zoom in and/or out either optically and/or digitally. Furthermore, each image capturing assembly 111 may be configurable to move in one or more directions and/or positions with respect to the head assembly 110, and may also protrude outwardly and/or retract inwardly with respect to the head assembly 110. In an example embodiment, the image capturing assembly 111 may be housed, either in part or in whole, in one or more portions of the endoscopic system 100, such as the head assembly 110.

Each image capturing assembly 111 may further comprise one or more illumination or light sources, such as an LED light source, optical fiber, and/or the like. It is to be understood in the present disclosure that each illumination source may be located together with and/or separate from the image capturing assembly 111 in example embodiments so as to improve illumination of the interior cavity of the patient. For example, in example embodiments, each illumination source may be provided as one or more illumination sources on the face 110c of the head assembly 110, one or more illumination sources distributed and/or continuously shaped around the perimeter of the face 110c of the head assembly 110 (such as a ring-shaped illumination source when the face 110c of the head assembly 110 has a circular shape), etc.

Each image capturing assembly 111 and/or each light source may receive power from a power source (not shown), and/or the like, and such power may be received via wires and/or wirelessly. In an example embodiment, the power source may be housed, either in part or in whole, in one or more portions of the endoscopic system 100, such as the head assembly 110, the main body 130, and/or the second main body 150, and/or provided outside of the patient (such as separate power source 180 and/or power obtained from controller 160).

Each image capturing assembly 111 may be configurable to provide captured/recorded images (such as still images and/or video images, hereinafter "captured images") to a controller 160, computer-readable medium 162, and/or the like, and such captured images may be received by the controller 160 and/or computer-readable medium 162 via wires and/or wirelessly. An operator/surgeon performing a diagnostic, therapeutic, and/or surgical procedure using the endoscopic system 100 may be operable to receive and view the captured images in real-time and/or near real-time via the controller 160, and such captured images may also be stored in the computer-readable medium 162 for viewing at a later time as well. In example embodiments, the operator/ surgeon may perform, among other things, one or more of the following using the captured images of the image capturing assembly 111: one or more insertions of a portion of the endoscopic system 100 into the cavity of the patient; one or more anchoring of the anchor assembly 120 and/or second anchor assembly 140; one or more advancing of the main body 130 and/or second main body 150; a straightening of one or more flexural or looping/bending sections of the cavity of the patient; illumination of one or more portions of the cavity of the patient via the light source of the head assembly 110; one or more diagnostic, therapeutic, and/or surgical procedures using one or more of the instruments 112; one or more other procedures and operations of the endoscopic system 100, or parts thereof; etc.

In an example embodiment, the controller 160 and/or computer-readable medium 162 may be housed, either in part or in whole, in one or more portions of the endoscopic system 100, such as the head assembly 110, the main body 130, and/or the second main body 150, and/or provided outside of the patient (as illustrated in at least FIG. 1, FIG. 6, and FIGS. 7A-B). The controller 160 may be any device or system operable to communicate with one or more elements of endoscopic system 100, and may include a computing device, communication device, processor, virtual machine, computer, node, instance, host, server, client, chip/microchip, and/or machine, including combinations thereof and/or those in a networked computing environment. The controller 160 may comprise logic stored in non-transitory computer readable medium, such as computer readable medium 162, which, when executed by the controller 160 and/or a processor of or associated with the controller 160, is operable to perform one or more actions, operations, configurations, and/or communications with one or more elements of the endoscopic system 100, including those described above and in the present disclosure. For example, the controller 160 may be operable to, among other things, communicate with and/or configure one or more of: the computer-readable medium 162, the image capturing assembly 111, instrument 112, movement control cavity 113, irrigation cavity 114, insufflation cavity 115, second end portion 110b, first end portion 110a, head assembly 110, first end 130a, main body 130, movement control cavity 133, irrigation cavity 134, insufflation cavity 135, anchor cavities 136, first end 150a, second main body 150, anchor cavities 154, first expandable member 124, second expandable member 122, first anchor assembly 120, third expandable member 144, fourth expandable member 142, second anchor assembly 140, first suction opening 126, second suction opening 146, pressure control subsystem 170, power source 180, irrigation subsystem 190, insufflation subsystem 192, expansion source subsystem 194, etc. Example embodiments of the controller 160 will be further described in the present disclosure, including in the below section "the controller (e.g., controller 160)".

Figure 2B:
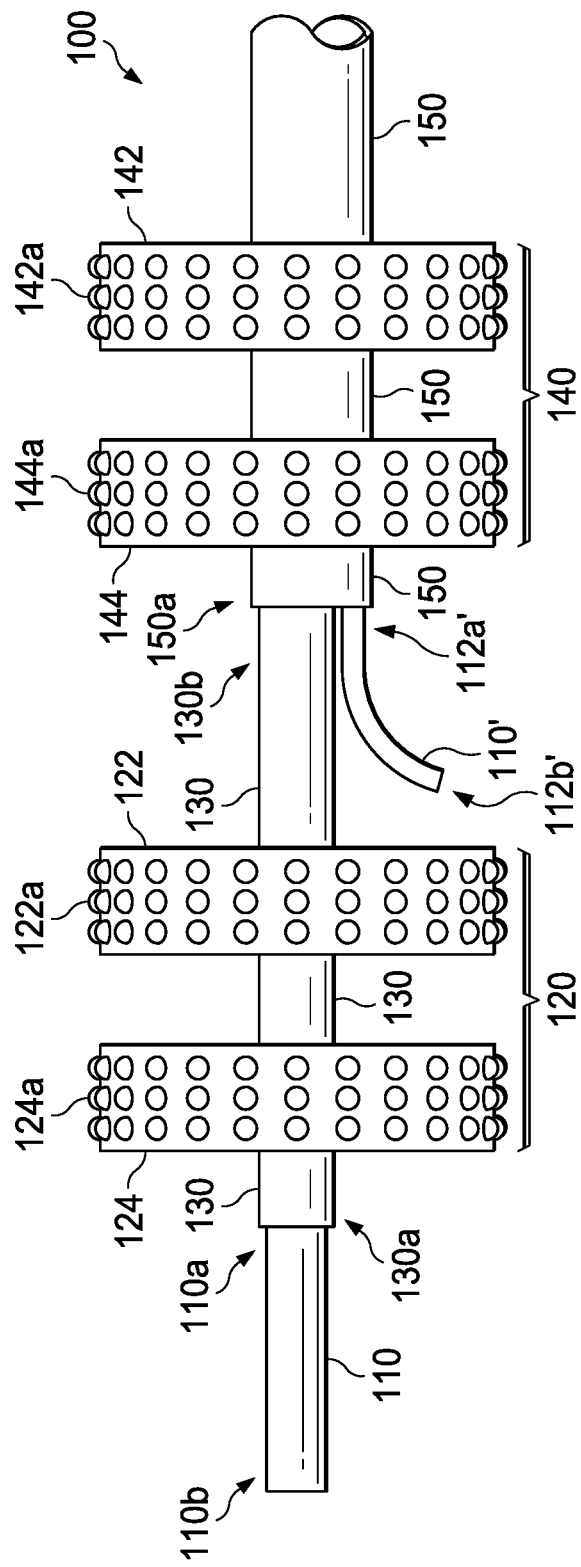
FIG. 2B is an illustration of a side view of an example embodiment of the endoscopic system.
Figure 2C:
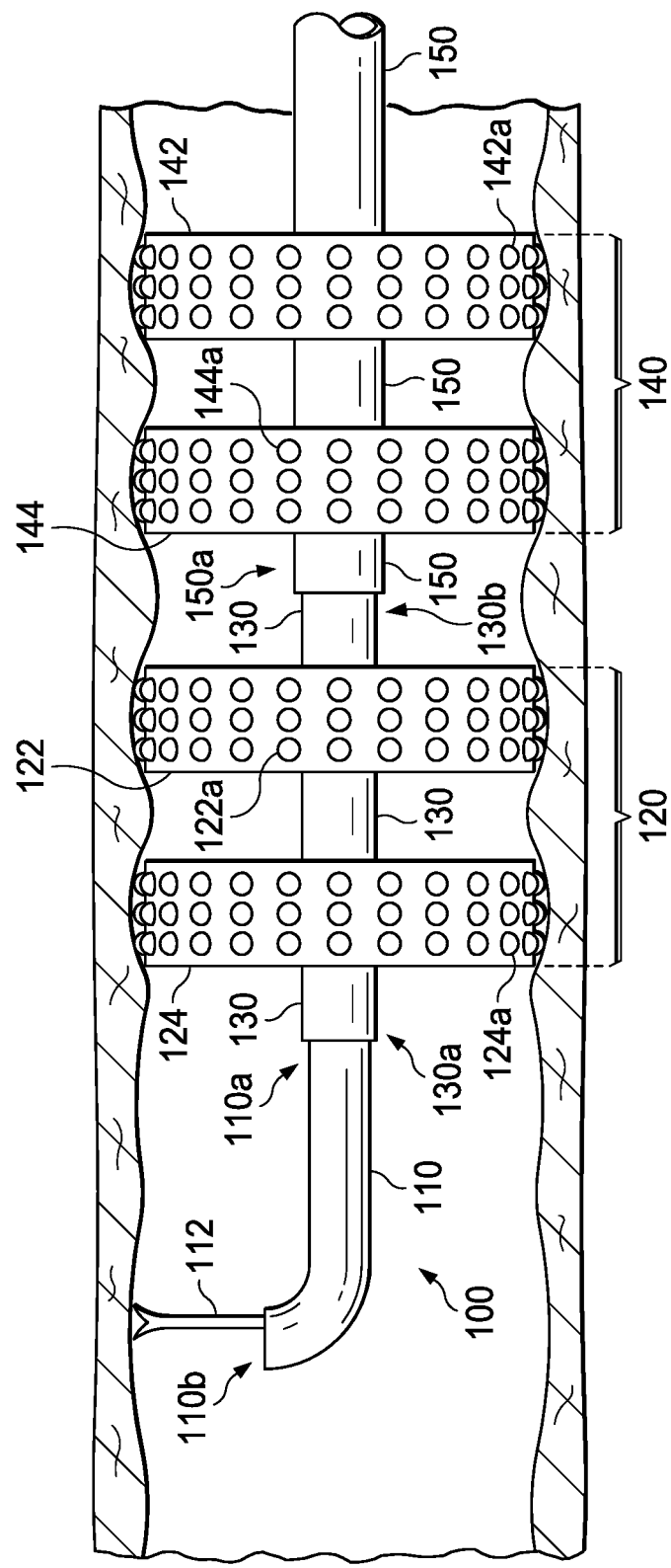
FIG. 2C is an illustration of a side view of an example embodiment of the endoscopic system in a cavity, such as a colonic lumen, of a patient.

As illustrated in at least FIG. 2C, the head assembly 110 may further comprise one or more instruments 112. Each instrument 112 may be any one or more surgical instruments, or the like, for use in performing a diagnostic, therapeutic, and/or surgical procedure, and/or obtaining samples. For example, each instrument 112 may include one or more biopsy forceps, miniaturized manipulator, snare, and/or the like. In example embodiments, the one or more instruments 112 may be housed in one or more portions of the endoscopic system 100, such as in the head assembly 110, the main body 130, the second main body 150, and/or outside of the cavity of the patient. When needed, the one or more instruments 112 may be provided through an instrument cavity or channel 112a (see FIGS. 1 and 2A), and may also be provided outwardly (as illustrated in at least FIG. 2C) and/or retracted inwardly with respect to the head assembly 110. In example embodiments, the instrument 112 may be configurable to have one or more degrees of freedom (DOF) of movement. The one or more instruments 112 may be configured and/or controlled by the controller 160 and/or an operator/surgeon, either manually and/or via the controller 160, in example embodiments. Furthermore, one or more movements and/or positions of the instrument(s) 112 may be stored in the computer-readable medium 162.

At least a portion of the head assembly 110, such as the second end portion 110b, may be selectively configurable to actuate (including bending, turning, pivoting, twisting, moving, etc., hereinafter "actuate") in one or more of a plurality of directions (and/or positions, locations, and/or the like) with respect to one or more points/areas, such as the first end portion 110a and/or other portions of the head assembly 110 and/or endoscopic system 100. For example, the second end portion 110b may be selectively configured and/or controlled to actuate (bend) in a plurality of directions, such as the bending illustrated in at least FIG. 3D and FIGS. 2A and 2C. The second end portion 110b may also be selectively configured and/or controlled to actuate (extend outwardly and/or retract inwardly) with respect to one or more points/areas, such as the first end portion 110a of the head assembly 110 and/or other portions of the head assembly 110 and/or endoscopic system 100, as illustrated in at least FIG. 2D and FIG. 2E. Furthermore, the head assembly 110 may be capable of at least two degrees of freedom (DOF) of movement, including a pitch and yaw movement. In example embodiments, each degree of freedom may have a bending angle of at least 110 degrees.

It is recognized in the present disclosure that actuating of at least a portion of the head assembly 110 may assist in enabling the endoscopic system 100 to advance around flexural and/or looping/bending sections of the cavity of the patient without forceful manual pushing against the interior wall forming the cavity, such as the colonic lumen, of the patient. It is further recognized in the present disclosure that actuating of at least a portion of the head assembly 110, including those described above and in the present disclosure, may enable the one or more image capturing assemblies 111 to improve image capturing capabilities. Furthermore, actuating of at least a portion of the head assembly 110, including those described above and in the present disclosure, may enable the one or more illumination sources to provide improved illumination to specific areas within the cavity of the patient. Furthermore, actuating of at least a portion of the head assembly 110, including those described above and in the present disclosure, may enable the one or more instruments 112 to more readily access and/or perform diagnostic, therapeutic, and/or surgical procedures, including obtaining samples, within the cavity of the patient and/or an interior wall forming the cavity of the patient.

The at least one portion of the head assembly 110 may be selectively configurable to actuate in one or more of a plurality of directions using one or more elements of the endoscopic system 100 and/or one or more methods described below and in the present disclosure. In an example embodiment, the head assembly 110 may comprise one or more movement control cavities 113, or the like. Each movement control cavity 113 may be operable to receive and/or house a filler, and/or the like. The filler may be any substance or material, including a gas, such as air, carbon dioxide, nitrogen, a liquid, such as water, oil, and/or a solid, such as micro particle. When it is desired to actuate a movement, control, and/or position of a portion of the head assembly 110, such as the second end portion 110*b* of the head assembly 110, in a specific desired direction and/or position, a predetermined selection and/or combination of one or more of the movement control cavities 113 may be selectively configured and controlled. For example, one or more of the movement control cavities 113 may house one or more types of fillers, and such fillers may be manipulated, manually by operator/surgeon and/or via controller 160, to actuate the portion of the head assembly 110. As another example, one or more of the movement control cavities 113 may be provided with a predetermined quantity of one or more types of fillers when actuating of the portion of the head assembly 110 is required. As another example, the properties of the filler material housed in one or more of the movement control cavities 113 may be selectively configured to change, such as change in volume (expand and/or contract), stiffen, become more flexible, change from gas to liquid phase (and vice versa), change from liquid to solid phase (and vice versa), change from gas to solid phase (and vice versa), change in pressure, change in temperature, change in shape, change in size, change in tensile strength, etc. To effect one or more such changes, the one or more fillers may be a material (or combination of materials) selected in such a way that an introduction, application, and/or removal of an application, each as applicable, of an electric current, voltage potential, resistance, pressure, temperature, magnetic field, and/or the like, causes and/or controls one or more of the above-mentioned changes in properties. For example, the filler may be a memory-shaped metal or other material, or the like.

In example embodiments, the actuating of the head assembly 110, including the second end portion 110*b* of the head assembly 110, as described above and in the present disclosure, may be performed and/or controlled by the controller 160 and/or an operator/surgeon, either manually and/or via the controller 160. Furthermore, the amount of filler, change in quantity of filler, and/or change in properties of the filler in the one or more movement control cavities 113 may be stored in the computer-readable medium 162.

It is to be understood in the present disclosure that very small/minute, precise/accurate, quick, and firm movements of the second end portion 110*b* of the head assembly 110, as well as the instrument(s) 112, image capturing assembly 111, and/or other portions of the endoscopic system 100, may be achievable using the aforementioned elements of the endoscopic system 100 and/or methods. It is also to be understood in the present disclosure that other elements and/or methods for actuating a movement, control, and/or position of a portion of the head assembly 110, such as one or more sensors (such as motion sensors, proximity sensors, distance sensors, etc.), are contemplated without departing from the teachings of the present disclosure. Furthermore, it is recognized in the present disclosure that movement, positioning, and/or controlling of other elements of the endoscopic system, including one or more of the instrument 112, main body 130, second main body 150, head assembly 110', and/or other elements of the endoscopic system 100 may also be based on, performed, and/or controlled in a similar and/or substantially the same manner as described above for the head assembly 110 in example embodiments.

As illustrated in at least FIGS. 1 and 2A, the head assembly 110 may further comprise one or more irrigation cavities 114. Each irrigation cavity 114 may be configurable to provide movement of fluid and/or solids into and/or out of the cavity of the patient via an irrigation subsystem 190. For example, each irrigation cavity 114 in communication with the irrigation subsystem 190 may be operable to introduce a liquid into the cavity of the patient, and each irrigation cavity 114 in communication with the irrigation subsystem 190 may be operable to remove a liquid, such as water, and/or solid, such as polyps, from the cavity of the patient. In example embodiments, the movement of fluid and/or solids into and/or out of the cavity of the patient via the one or more irrigation cavities 114 may be performed and/or controlled by the controller 160 and/or an operator/surgeon, either manually and/or via the controller 160. Furthermore, the amount of such movements of liquid and/or solids into and/or out of the cavity of the patient via the one or more irrigation cavities 114 may be stored in the computer-readable medium 162.

The head assembly 110 may further comprise one or more insufflation cavities 115. Each insufflation cavity 115 may be configurable to provide a gas for use in performing insufflation of the cavity of the patient via an insufflation subsystem 192. In example embodiments, the insufflation of the cavity of the patient via the one or more insufflation cavities 115 may be performed and/or controlled by the controller 160 and/or an operator/surgeon either manually and/or via the controller 160. Furthermore, the amount of such insufflation via the one or more insufflation cavities 115 may be stored in the computer-readable medium 162.

It is to be understood in the present disclosure that the head assembly 110, including one or more of the image capturing assembly 111, illumination source, instrument 112, movement control cavities 113, irrigation cavity 114, irrigation subsystem 190, insufflation cavity 115, and/or insufflation subsystem 192 may be provided in a configuration that is the same as, similar to, based on, or different from that illustrated in the example embodiment of FIGS. 1 and 2A without departing from the teachings of the present disclosure. Furthermore, one or more of the image capturing assembly 111, illumination source, instrument 112, movement control cavities 113, irrigation cavity 114, and insufflation cavity 115 may be provided, or not provided, in the head assembly 110 without departing from the teachings of the present disclosure.

The head assembly 110, and/or cross-section thereof, may be formed in any one of a plurality of shapes, sizes, and/or dimensions. For example, the head assembly 110 may be an elongated cylindrical body, as illustrated in FIGS. 1 and 2A. The cross-sectional shape of the head assembly 110 may also be one or more of a rectangle, square, pentagon, hexagon, etc., or combination of one or more geometric shapes, without departing from the teachings of the present disclosure.

In an example embodiment wherein the shape of the head assembly 110 is cylindrical in shape with a circular cross-section, an outer diameter of the cross-section of the head assembly 110 may be between about 5 to 30 mm. The length of the head assembly 110 may be between about 10 to 100 mm. It is to be understood in the present disclosure that the above dimensions are merely an illustration of example embodiments, and as such the dimensions may be smaller or larger than those recited above without departing from the teachings of the present disclosure.

The head assembly 110 may be formed using any one or more of a plurality of materials, such as surgical-grade plastics, rubbers, etc. The instrument 112 may be formed using any one or more of a plurality of materials, such as surgical-grade metals, high-strength aluminum alloys, stainless steel (such as 304/304L, 316/316L, and 420), pure titanium, titanium alloys (such as $Ti_6Al_4V$, NiTi), cobalt-chromium alloys, etc. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Main Body (e.g., Main Body 130)

FIG. 1, FIGS. 2A-C, and FIGS. 3A-H illustrate an example embodiment of the main body 130 of the endoscopic system 100. As used in the present disclosure, the main body 130 may also be referred to as the first main body 130, inner body 130, first tube 130, inner tube 130, and/or the like. The main body 130 may comprise a first end 130*a* and an exposed end portion 130*b*. The first end 130*a* of the main body 130 may be attachable to the first end portion 110*a* of the head assembly 110 in example embodiments. During diagnostic and/or therapeutic/surgical procedures, the first end 130*a* may be fixedly attached to the first end portion 110*a* of the head assembly 110, as illustrated in at least FIGS. 1 to 3.

Figure 3A:
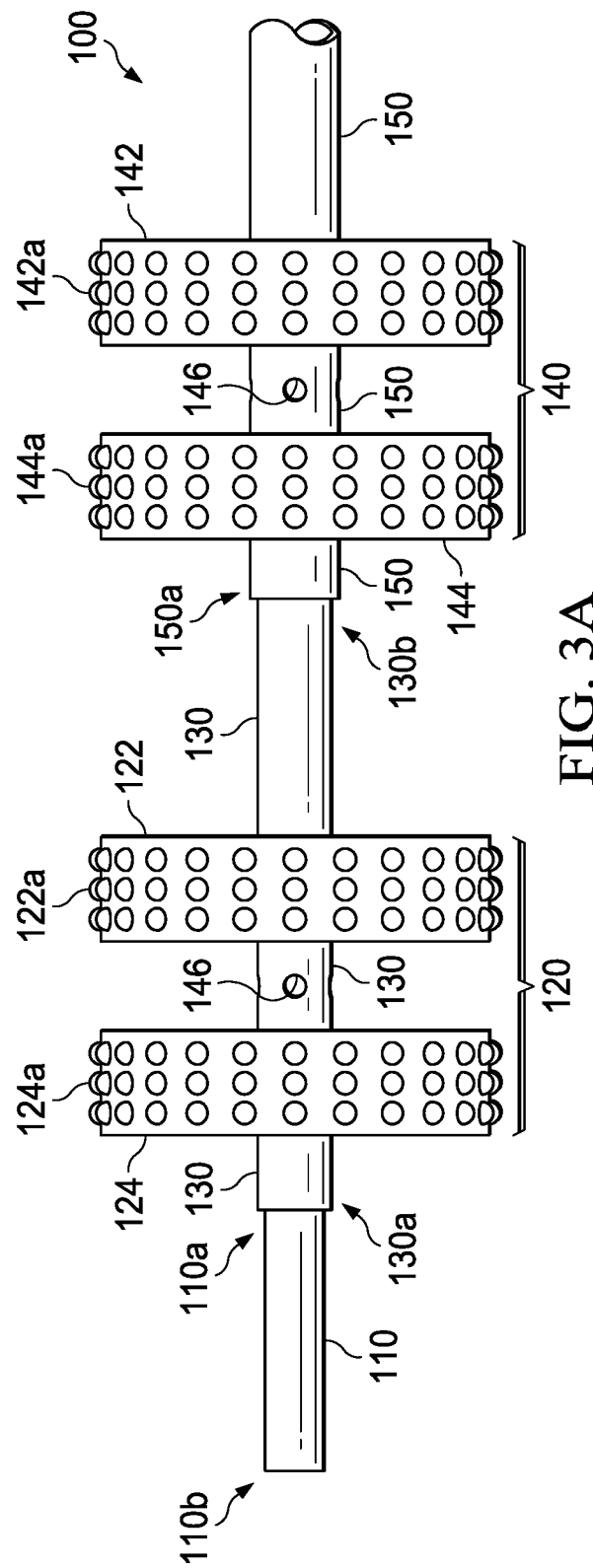
FIG. 3A is an illustration of a side view of an example embodiment of the endoscopic system.
Figure 3B:
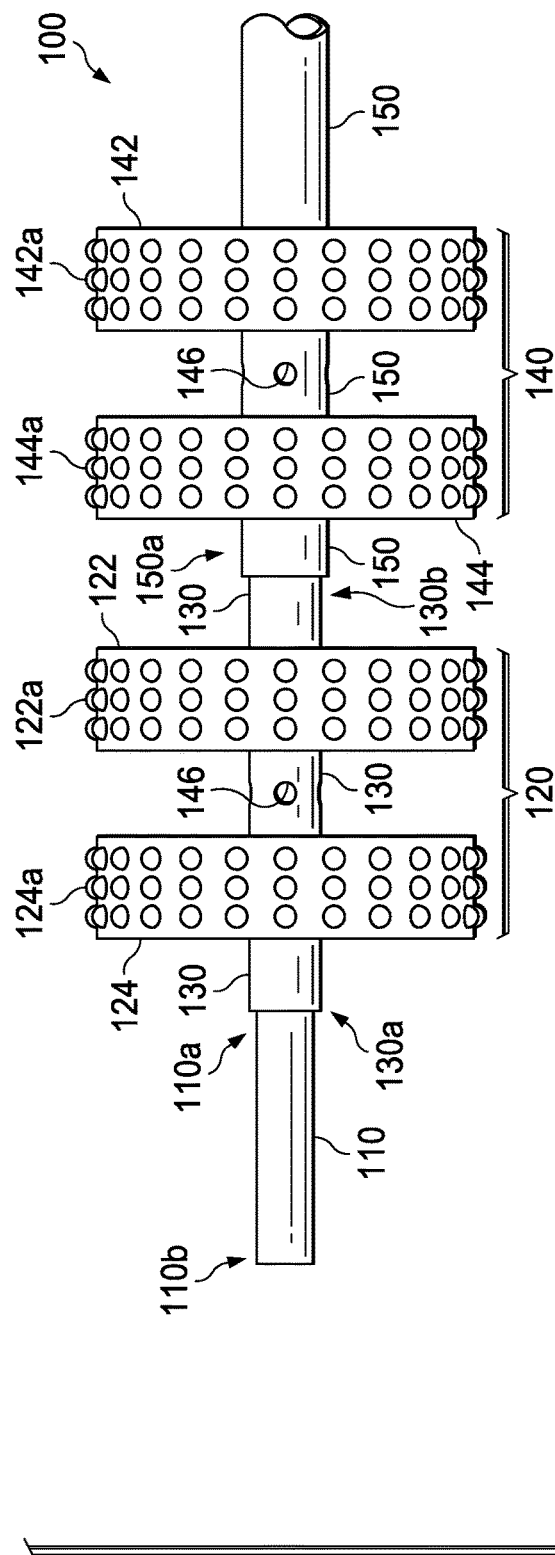
FIG. 3B is an illustration of a side view of an example embodiment of the endoscopic system.
Figure 3B:
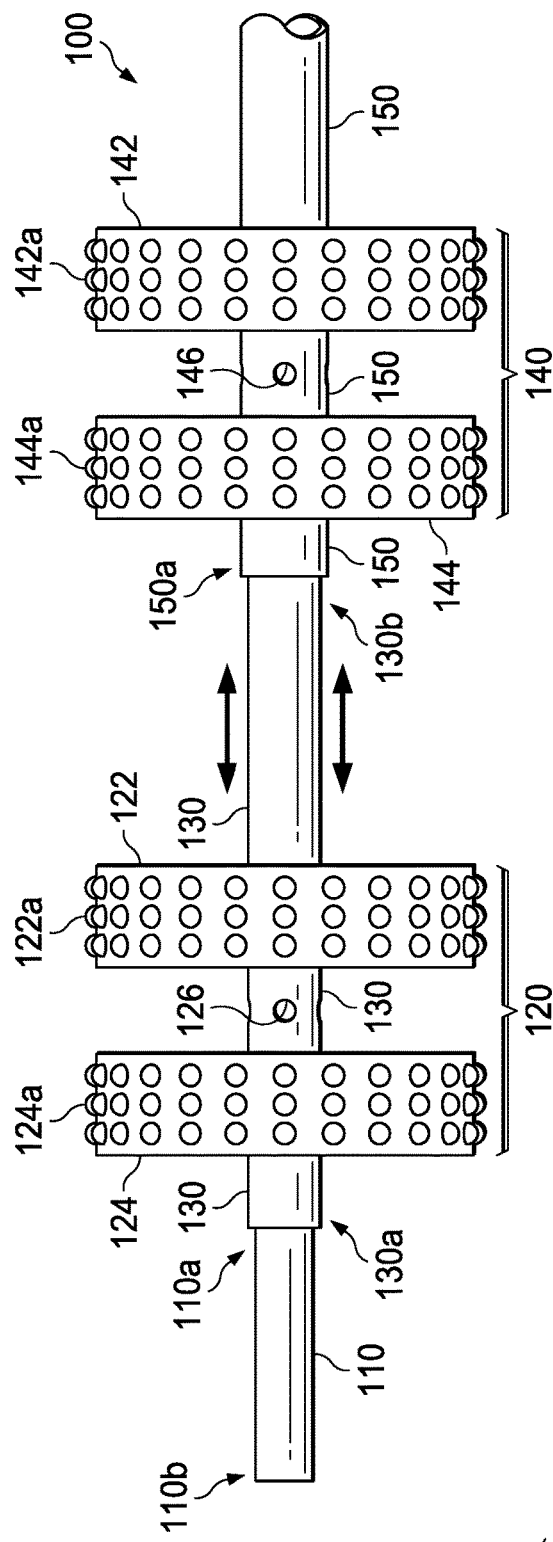

At least a portion of the main body 130 may be selectively configurable to actuate (and/or bend, turn, pivot, twist, move, and/or the like) in one or more of a plurality of directions (and/or positions, locations, and/or the like) with respect to the second main body 150 and/or other portions of the main body 130 and/or endoscopic system 100. Such actuating of a portion of the main body 130 may be similar to, the same as, based on, or different from the actuating described above for the head assembly 110. For example, a portion of the main body 130 closer to the first end 130*a* may be selectively configured and/or controlled to bend in a plurality of directions, as illustrated in at least FIG. 3E and FIG. 1. The said portion of the main body 130 closer to the first end 130*a* may also be selectively configured and/or controlled to slide, that is, extend outwardly and/or retract inwardly, with respect to the second main body 150 in example embodiments, as illustrated in FIG. 3B. It is recognized in the present disclosure that sliding and/or actuating of at least a portion of the main body 130 may enable the endoscopic system 100 to advance around flexural and/or looping/bending sections of the cavity of the patient without forceful manual pushing against the interior wall forming the cavity of the patient. Furthermore, actuating of at least a portion of the main body 130 may enable the one or more illumination sources of the head assembly 110 to provide improved illumination to specific areas within the cavity of the patient. Furthermore, actuating of at least a portion of the main body 130 may enable the one or more instruments 112 of the head assembly 110 to more readily access and perform diagnostic, therapeutic and/or surgical procedures, including obtaining samples, within the cavity of the patient.

Figure 3C:
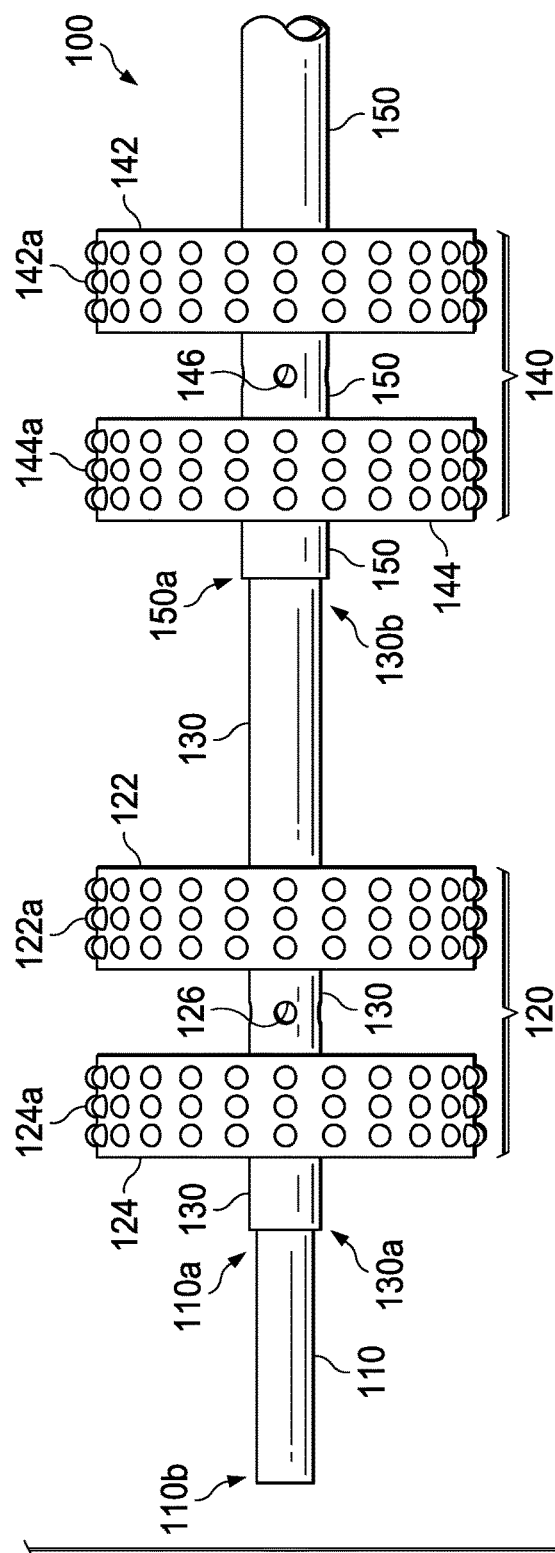
FIG. 3C is an illustration of a side view of an example embodiment of the endoscopic system.
Figure 3C:
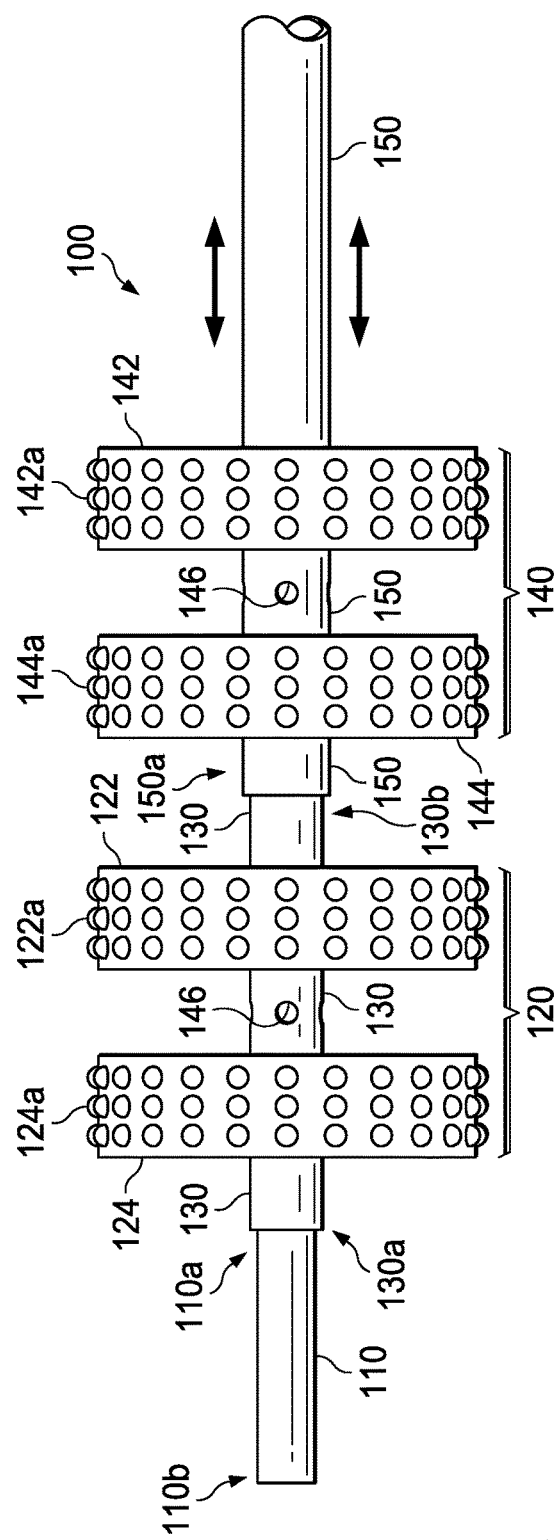

At least one portion of the main body 130 may be selectively configurable to slide with respect to the second main body 150 (as illustrated in FIGS. 3B-C) and/or actuate in one or more of a plurality of directions using one or more elements of the endoscopic system 100 and/or one or more methods, as described below and in the present disclosure. In an example embodiment illustrated in FIG. 3H, the main body 130 may comprise one or more movement control cavities 133, or the like. Each movement control cavity 133 may be operable to receive and/or house a filler, and/or the like. The filler may be any substance or material, including a gas, such as air, carbon dioxide, nitrogen, a liquid, such as water, oil, and/or a solid, such as micro particle. When it is desired to actuate a movement, control, and/or position of a portion of the main body 130, such as the portion of the main body 130 closer to the first end 130*a*, in a specific desired direction and/or position, a predetermined selection and/or combination of one or more of the movement control cavities 133 may be selectively configured and controlled. For example, one or more of the movement control cavities 133 may house one or more types of fillers, such as gas, and such fillers may be manipulated, manually by operator/surgeon and/or via controller 160, to actuate the portion of the main body 130, such as via the pressure control subsystem 170, expansion source subsystem 194, etc. As another example, one or more of the movement control cavities 133 may be provided with a predetermined quantity of one or more types of fillers when actuating of the portion of the main body 130 is required. As another example, the properties of the filler material housed in one or more of the movement control cavities 133 may be selectively configured to change, such as change in volume (expand and/or contract), stiffen, become more flexible, change from gas to liquid phase (and vice versa), change from liquid to solid phase (and vice versa), change from gas to solid phase (and vice versa), change in pressure, change in temperature, change in shape/size, change in tensile strength, etc. To effect one or more such changes, the one or more fillers may be a material (or combination of materials) selected in such a way that an introduction, application, change, and/or removal of an application, each as applicable, of an electric current, voltage potential, resistance, pressure, temperature, magnetic field, and/or the like, causes one or more of the above-mentioned changes in properties. For example, the filler may be a memory-shaped metal, other material, spring-based or spring-like material, or the like.

In example embodiments, the actuating of the main body 130, including the portion of the main body 130 closer to the first end 130*a*, as described above and in the present disclosure, may be performed and/or controlled by the controller 160 and/or an operator/surgeon, either manually and/or via the controller 160. Furthermore, the amount of filler, change in quantity of filler, and/or change in properties of the filler in the one or more movement control cavities 133 may be stored in the computer-readable medium 162.

It is to be understood in the present disclosure that very small/minute, precise/accurate, quick, and firm movements of the portion of the main body 130 closer to the first end 130*a*, may be achievable using the aforementioned elements of the endoscopic system 100 and/or methods. It is also to be understood in the present disclosure that other elements and/or methods for actuating a movement, control, and/or position of a portion of the main body 130 and/or other elements of the endoscopic system 100 are contemplated without departing from the teachings of the present disclosure. Furthermore, it is recognized in the present disclosure that movement, positioning, and/or controlling of other elements of the endoscopic system, including one or more of the instrument 112, head assembly 110, second main body 150, and/or other elements of the endoscopic system 100 may also be based on, performed, and/or controlled in a similar and/or substantially the same manner as described above for the main body 130 in example embodiments.

Figure 3D:
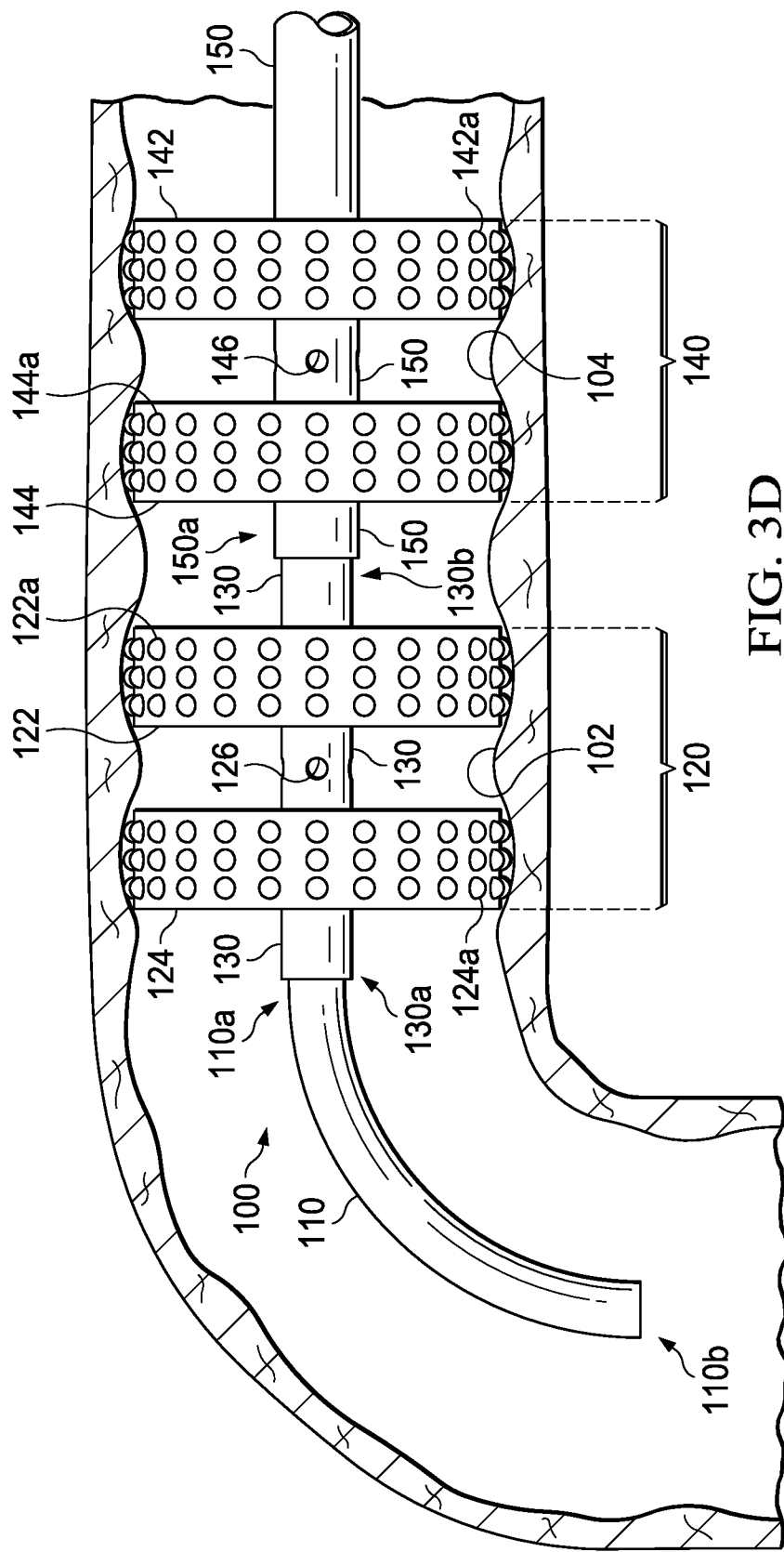
FIG. 3D is an illustration of a side view of an example embodiment of the endoscopic system in a cavity of a patient, and the head assembly bending based on a bend in the cavity of the patient.
Figure 3E:
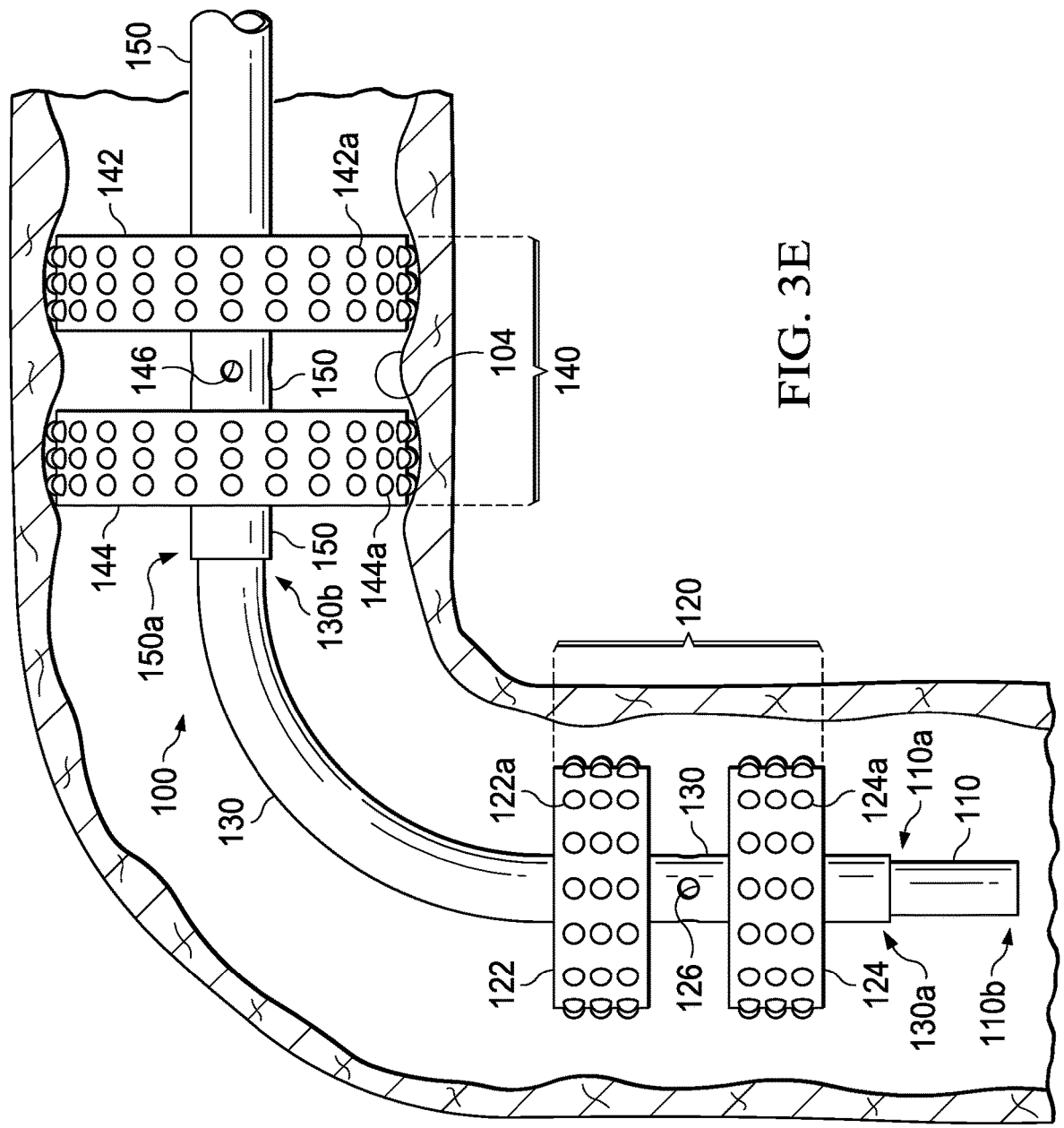
FIG. 3E is an illustration of a side view of an example embodiment of the endoscopic system, and the first main body bending based on the bend in the cavity of the patient.
Figure 3F:
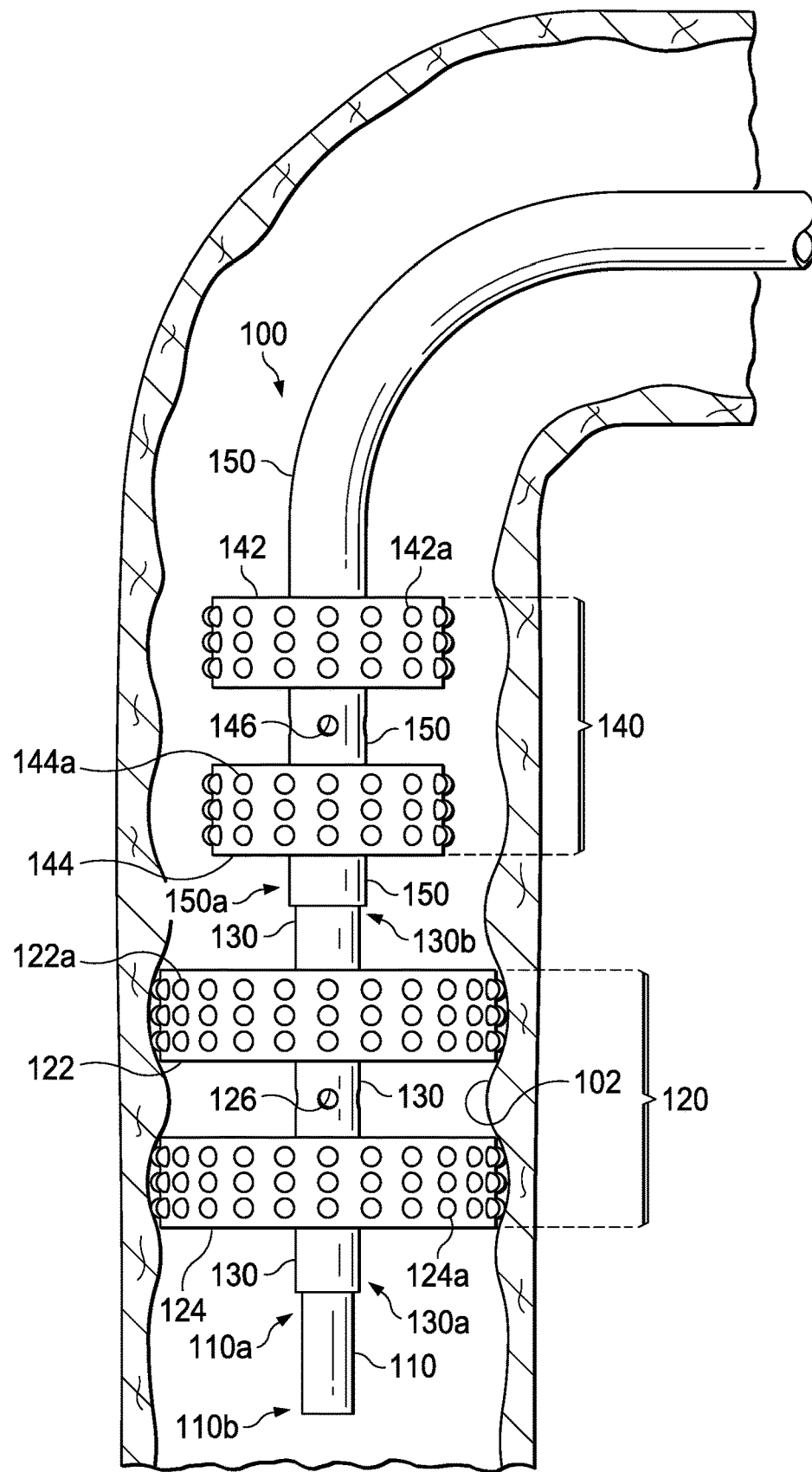
FIG. 3F is an illustration of a side view of an example embodiment of the endoscopic system, and the second main body bending based on the bend in the cavity of the patient.
Figure 3G:
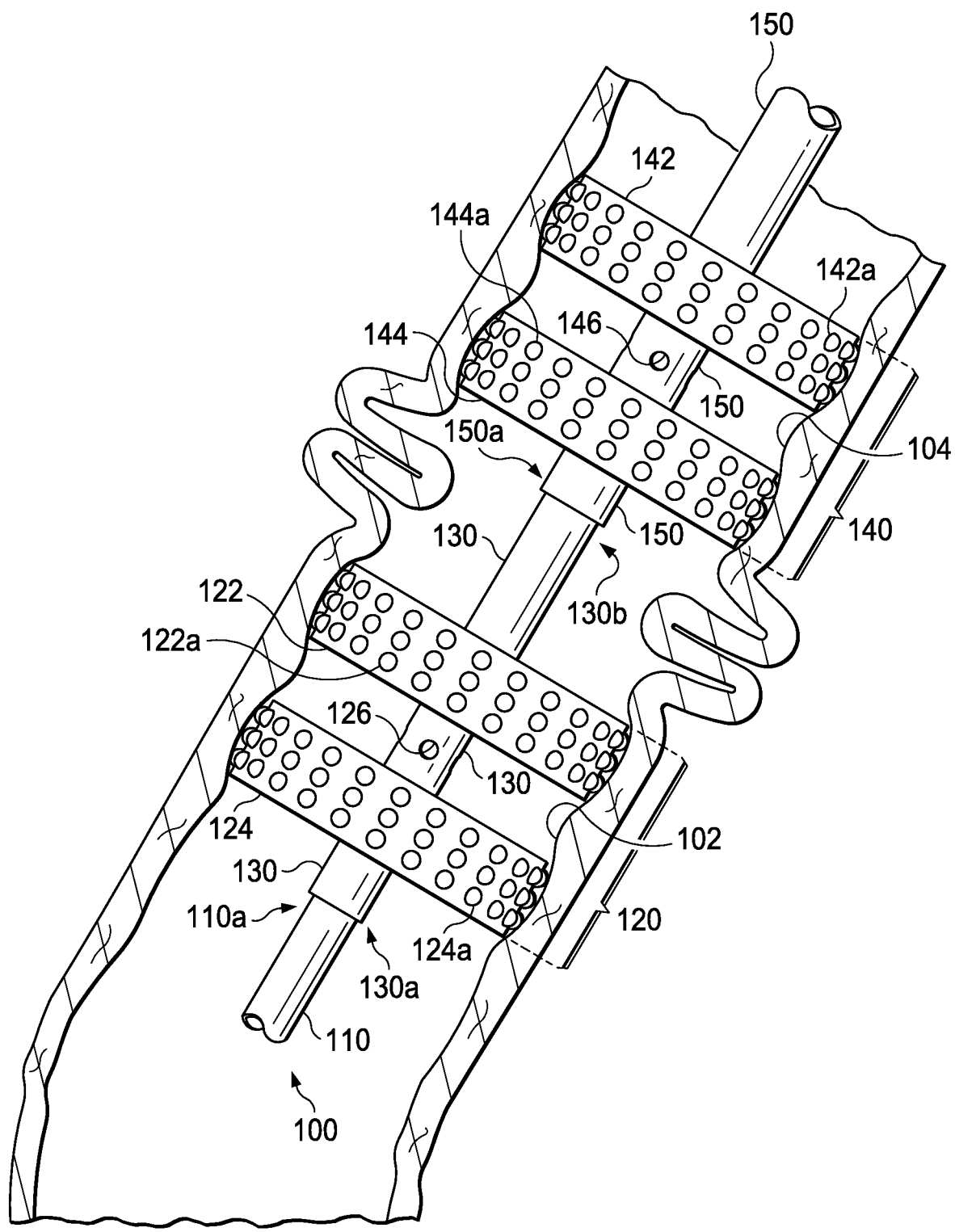
FIG. 3G is an illustration of a side view of an example embodiment of the endoscopic system, and the straightening of the flexural and/or looping/bending section in the cavity of the patient.
Figure 3H:
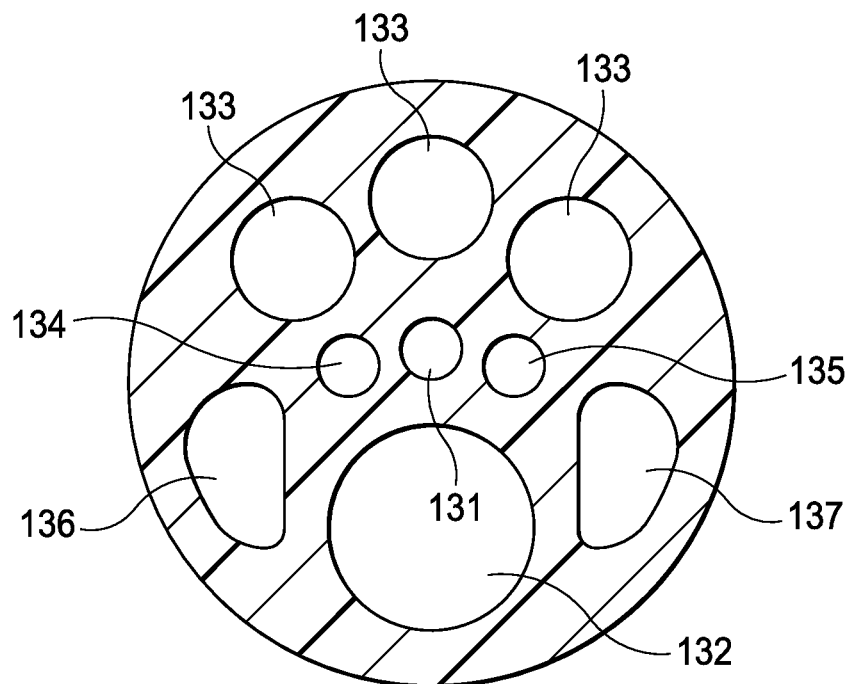
FIG. 3H is an illustration of a cross-sectional view of an example embodiment of the first main body.

As illustrated in at least FIG. 3H, in example embodiments, the main body 130 may further comprise one or more image capturing cavities 131. The image capturing cavity 131 may be operable to enable the image capturing assembly 111 and/or other image capturing assemblies (such as those in head assembly 110') to move with respect to the head assembly 110, and/or enable cables (if any) of the image capturing assembly 111 and/or other image capturing assemblies (such as those in head assembly 110') to be connected to the controller 160 and/or computer-readable medium 162.

As illustrated in at least FIG. 3H, in example embodiments, the main body 130 may further comprise one or more instrument cavities 132. The instrument cavity 132 may be operable to enable the instrument 112 and/or other instruments (not shown) to move with respect to the head assembly (i.e., connected to the instrument cavity 112a), and/or enable cables (if any) and/or connections (if any) of the instrument 112 to be accessible by the operator/surgeon and/or connected to the controller 160 and/or computer-readable medium 162.

As illustrated in at least FIG. 3H, in example embodiments, the main body 130 may further comprise one or more irrigation cavities 134. The irrigation cavity 134 may be operable to enable the movement of fluid and/or solids into and/or out of the cavity of the patient. The irrigation cavity 134 may be connected to the irrigation cavity 114 and/or other irrigation cavities and/or openings (not shown). The irrigation cavity 134 may also be connected to the irrigation subsystem 190 in example embodiments.

As illustrated in at least FIG. 3H, in example embodiments, the main body 130 may further comprise one or more insufflation cavities 135. The insufflation cavity 135 may be operable to provide a gas for use in performing insufflation of the cavity of the patient. The insufflation cavity 135 may or may not be connected to the insufflation cavity 115. The insufflation cavity 135 may also be connected to the insufflation subsystem 192 or a different subsystem in example embodiments.

As illustrated in at least FIG. 3H, in example embodiments, the main body 130 may further comprise one or more anchor cavities 136 operable to configure, control, and/or assist in configuring and/or controlling the anchor assembly 120. The anchor cavity 136 may be operable to provide a gas, liquid, and/or solid, and/or combination thereof, for use in expanding (such as expanding radially from the main body 130) one or more of the first expandable member 122 and the second expandable member 124. The anchor cavity 136 may be connected to one or more of the first expandable member 122 and the second expandable member 124. The anchor cavity 136 may also be connected to an expansion source subsystem 194 in example embodiments. The anchor assembly 120 will be further described below.

As illustrated in at least FIG. 3H, in example embodiments, the main body 130 may further comprise one or more suction cavities 137. The suction cavity 137 may be operable to provide a negative pressure (or perform a removal of gas). For example, the suction cavity 137 may be operable to apply a negative pressure to a region between the first expandable member 122 (when expanded), the second expandable member 124 (when expanded), the interior wall forming the cavity of the patient 102, and the main body 130. The suction cavity 137 may be connected to the suction opening 126. The suction cavity 137 may also be connected to the pressure control subsystem 170 in example embodiments. The suction opening 126 will be further described below.

It is to be understood in the present disclosure that the main body 130, including one or more of the image capturing cavities 131, instrument cavities 132, movement control cavities 133, irrigation cavity 134, irrigation subsystem 190, insufflation cavity 135, insufflation subsystem 192, anchor cavities 136, expansion source subsystem 194, suction cavities 137, and pressure control subsystem 170 may be provided in a configuration that is the same as, similar to, based on, or different from that illustrated in the example embodiment of FIG. 3H without departing from the teachings of the present disclosure. Furthermore, one or more of the image capturing cavities 131, instrument cavities 132, movement control cavities 133, irrigation cavity 134, insufflation cavity 135, anchor cavities 136, and suction cavities 137 may be provided, or not provided, in the main body 130 without departing from the teachings of the present disclosure. It is also to be understood in the present disclosure that one or more of the irrigation subsystem 190, insufflation subsystem 192, expansion source subsystem 194, and pressure control subsystem 170 may be the same or different subsystems in example embodiments.

The main body 130, and cross-section thereof, may be formed in any one of a plurality of shapes, sizes, and/or dimensions. For example, the main body 130 may be an elongated cylindrical body, as illustrated in FIGS. 1 to 3. A cross sectional shape of the main body 130 may also be one or more of a rectangle, square, pentagon, hexagon, etc., or combination of one or more geometric shapes, without departing from the teachings of the present disclosure.

In an example embodiment wherein the cross-sectional shape of the main body 130 is cylindrical in shape with a circular cross-section, an outer diameter of the main body 130 may be between about 5 to 30 mm. The length of the main body 130 may be expanded/contracted between about 50 to 200 cm. It is to be understood in the present disclosure that the above dimensions are merely an illustration of example embodiments, and as such the dimensions may be smaller or larger than those recited above without departing from the teachings of the present disclosure.

The main body 130 may be formed using any one or more of a plurality of materials, such as surgical-grade plastics, rubbers, etc. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Anchor Assembly (e.g., Anchor Assembly 120)

A perspective view of an example embodiment of an expanded anchor assembly 120 (e.g., anchor assembly 120 expanded radially from the main body 130) is illustrated in at least FIG. 1 and FIG. 2A; a side view of an example embodiment of an expanded anchor assembly 120 (e.g., anchor assembly 120 expanded radially from the main body 130) is illustrated in at least FIGS. 2B-C, FIG. 3A, FIG. 3D, and FIGS. 3F-G; and a side view of an example embodiment of an un-expanded anchor assembly 120 (e.g., anchor assembly 120 not expanded radially from the main body 130) is illustrated in at least FIGS. 3B-C. The anchor assembly 120 may be attachable to the main body 130. During diagnostic and/or therapeutic/surgical procedures, the anchor assembly 120 may be fixedly attached to the main body 130 near the first end 130a of the main body 130.

The anchor assembly 120 may be configurable to perform, among other things, a securing of a position and/or location of the main body 130. In an example embodiment, when the endoscopic system 100 is inserted into the cavity of the patient, as illustrated in at least FIG. 2C, FIG. 3D, and FIGS. 3F-G, the anchor assembly 120 may be configurable to secure the main body 130 with respect to the interior wall forming the cavity of the patient. The anchor assembly 120 may secure the main body 130 with respect to the interior wall forming the cavity of the patient in one or more of a plurality of ways. In an example embodiment, one or more expandable members 122, 124 may be expanded to contact the interior walls forming the cavity of the patient. The anchor assembly 120 may also secure the main body 130 with respect to the interior wall forming the cavity of the patient by applying a negative pressure via one or more suction openings 126. The anchor assembly 120 may also secure the main body 130 with respect to the interior wall forming the cavity of the patient via one or more surface patterns, roughness, protrusions, and/or the like formed on a surface, or portion(s) thereof, of one or more expandable members 122, 124. The anchor assembly 120 may also secure the main body 130 with respect to the interior wall forming the cavity of the patient using a magnetic element and corresponding external magnetic element provided outside of the patient. The securing, by the anchor assembly 120, of the main body 130 with respect to the interior wall forming the cavity of the patient will now be further described below.

The anchor assembly 120 may comprise one or more expandable members 122, 124. During diagnostic and/or therapeutic/surgical procedures, the one or more expandable members 122, 124 may be fixedly attached to the main body 130 near the first end 130a of the main body 130. In an example embodiment, the anchor assembly 120 may comprise expandable member 122. As used in the present disclosure, the expandable member 122 may also be referred to as the first expandable member 122, first balloon 122, and/or the like. The anchor assembly 120 may further comprise second expandable member 124. The second expandable member 124 may be provided between the first expandable member 122 and the first end 130a of the main body 130. As used in the present disclosure, the second expandable member 124 may also be referred to as the expandable member 124, second balloon 124, and/or the like. It is to be understood in the present disclosure that the anchor assembly 120 may comprise other quantities of expandable members, such as one or more additional expandable members, without departing from the teachings of the present disclosure.

Each expandable member 122, 124 may be configurable to change its volume/size to be a minimum volume/size, a maximum volume/size, and a volume/size between the minimum and maximum volumes/sizes. For example, each expandable member 122, 124 may be configurable to expand radially away from the main body 130.

In an example embodiment, each expandable member 122, 124 may be a hollow member resembling a balloon, tire, or the like. In this regard, each expandable member 122, 124 may be operable to expand (i.e., secure the main body 130) by receiving a gas (or positive pressure), liquid, solid, and/or combination thereof. The expanding of the expandable member 122, 124 may occur partially, substantially, or completely in a direction away from the main body 130 (i.e., radially away from the main body 130). Furthermore, each expandable member 122, 124 may be operable to reduce in size (or contract or un-secure the main body 130) by removing the gas (or removing the positive pressure or applying a negative pressure), liquid, solid, and/or combination thereof, received in the expandable member 122, 124. To secure the main body 130 with respect to the interior wall forming the cavity of the patient, the one or more expandable members 122, 124 may be expanded to contact the interior wall forming the cavity of the patient. It is recognized in the present disclosure that the expanding and contacting of the one or more expandable members 122, 124 with the interior wall forming the cavity of the patient may provide for a sufficient securing or anchoring of the main body 130 so as to withstand a force of at least 0.1 to 20 N.

One or more of the expandable members 122, 124 may comprise one or more surface patterns, roughness, protrusions, and/or the like formed on a surface, or portion(s) thereof, of the one or more expandable members 122, 124. During diagnostic and/or therapeutic/surgical procedures wherein a securing or anchoring of the main body 130 with respect to the interior wall forming the cavity of the patient is desired or required, such surface patterns, roughness, protrusions, and/or the like formed on the surface of one or more expandable members 122, 124 that are in contact with the interior wall forming the cavity of the patient may further improve the securing or anchoring of the main body 130. For example, the surface pattern, roughness, protrusions, and/or the like may provide, or contribute in providing, resistance of a movement of one or more of the expandable members 122, 124 contacting the interior wall forming the cavity of the patient with respect to the interior wall forming the cavity of the patient. It is recognized in the present disclosure that such securing or anchoring of the main body 130 may be operable to withstand a force of at least 0.1 to 30 N.

It is to be understood in the present disclosure that the anchor assembly 120, including one or more of the first and second expandable members 122, 124, may or may not be a hollow member resembling a balloon, tire, or the like. For example, one or more of the first and second expandable members 122, 124 may only be partially hollow. As another example, one or more of the first and second expandable members 122, 124 may be formed partially, substantially, and/or entirely of an expandable solid and/or liquid. In this regard, the properties of such material forming one or more of the first and second expandable members 122, 124 may be selectively configured to change, such as change in volume (expand and/or contract), stiffen, become more flexible, change from gas to liquid phase (and vice versa), change from liquid to solid phase (and vice versa), change from gas to solid phase (and vice versa), change in pressure, change in temperature, change in shape, change in size, change in tensile strength, etc. To effect one or more such changes, such material forming one or more of the first and second expandable members 122, 124 may be a material (or combination of materials) selected in such a way that an introduction, application, change, and/or removal of an application, each as applicable, of an electric current, voltage potential, resistance, pressure, temperature, magnetic field, and/or the like, causes one or more of the above-mentioned changes in properties. For example, such material may be a memory-shaped metal, other material, spring-based or spring-like material, or the like.

Figure 4A:
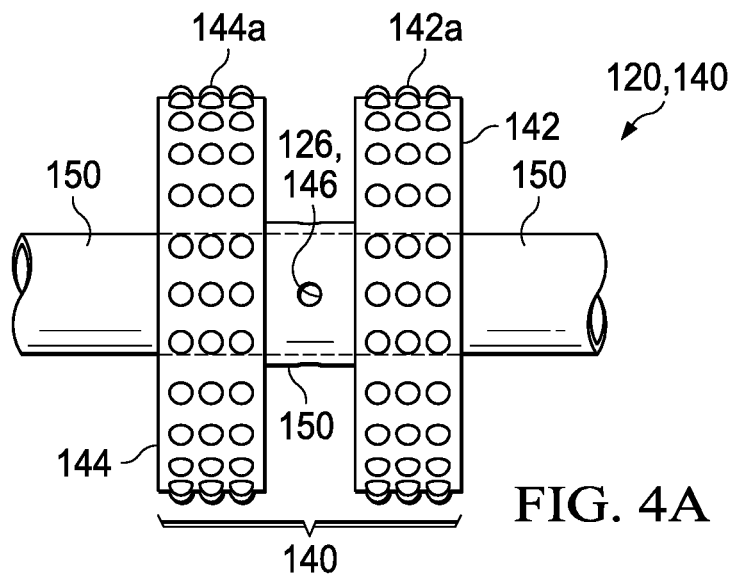
FIG. 4A is an illustration of a side view of an example embodiment of a first and/or second anchor assembly.
Figure 4B:
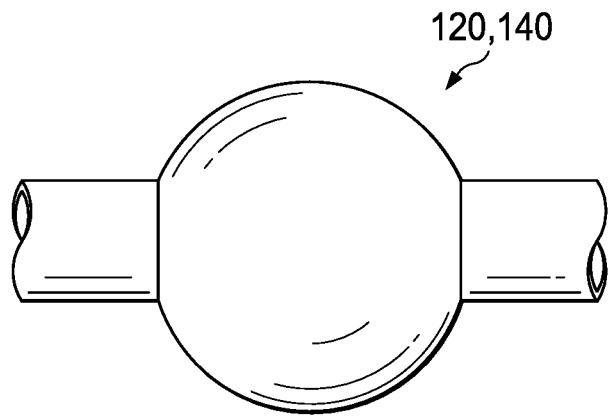
FIG. 4B is an illustration of a side view of another example embodiment of the first and/or second anchor assembly.
Figure 4C:
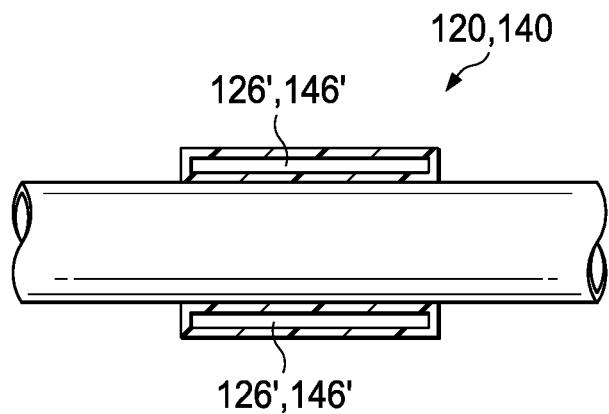
FIG. 4C is an illustration of a side view of another example embodiment of the first and/or second anchor assembly.

In some example embodiments, the anchor assembly 120 may comprise one or more expandable members that expand in one or more other directions in addition to expanding radially away from the main body 130, such as the example illustrated in FIG. 4B. In other example embodiments, such as the example illustrated in FIG. 4A, the anchor assembly 120 may comprise an integrated first and second expandable members 122, 124, or the like. In other example embodiments, such as the example illustrated in FIG. 4C, the anchor assembly 120 may comprise a magnetic element 126', or the like, operable to secure to a corresponding magnetic element provided outside of the patient.

Figure 4D:
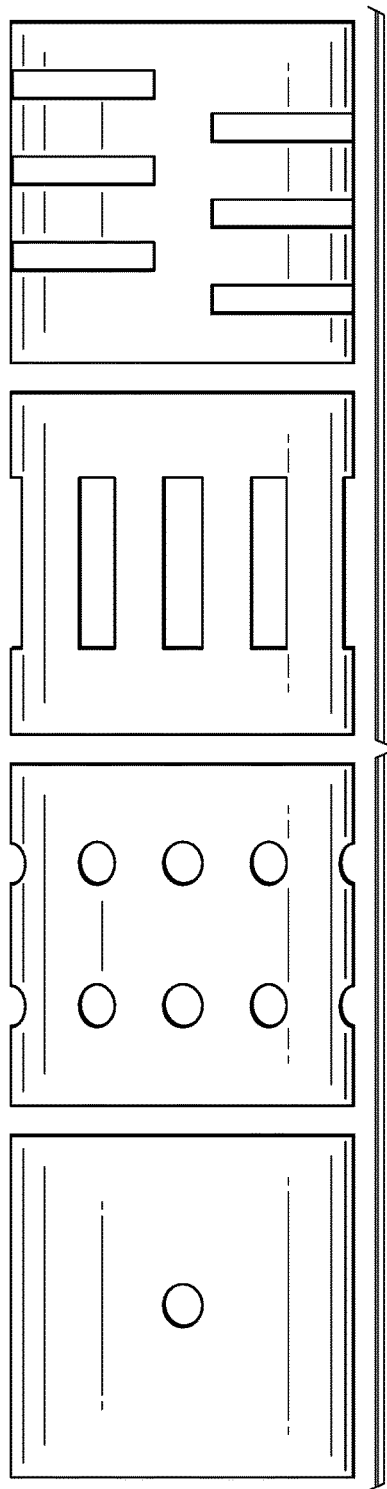
FIG. 4D is an illustration of a side view of example embodiments of the suction openings.

The anchor assembly 120 may further comprise one or more suction openings 126. As used in the present disclosure, the suction opening 126 may also be referred to as the first suction opening 126. The suction opening 126 may be formed in one or more of a plurality of shapes and provided in one or more quantities. FIG. 4D illustrates example embodiments of the one or more suction openings 126.

During diagnostic and/or therapeutic/surgical procedures wherein a securing or anchoring of the main body 130 with respect to the interior wall forming the cavity of the patient is desired or required, the one or more suction openings 126 may further improve the securing or anchoring of the main body 130. For example, the suction opening 126 may be operable to apply a negative pressure to a region between the first expandable member 122 (when expanded), the second expandable member 124 (when expanded), the interior wall forming the cavity of the patient 102 (as illustrated in at least FIG. 3F), and the main body 130. In example embodiments, the suction opening 126 may be configurable to apply a negative pressure and vary the applied negative pressure between about −10 kPa to vacuum. It is recognized in the present disclosure that such securing or anchoring of the main body 130 with the use of the expanded first and second expandable members 122, 124 and the one or more suction openings 126 may provide improved securing or anchoring, and may be operable to withstand a force of at least 0.1 to 40 N.

In example embodiments, the applying of the negative pressure by the suction opening 126 (i.e., the suctioning or removal of gas from the region between the first expandable member 122 (when expanded), the second expandable member 124 (when expanded), the interior wall forming the cavity of the patient 102, and the main body 130) may be performed prior to, at the same time as (or correspond with), and/or after the expansion of the expandable members 122, 124. Furthermore, in example embodiments, the applying of the negative pressure by the suction opening 126 (i.e., the suctioning or removal of gas from the region between the first expandable member 122 (when expanded), the second expandable member 124 (when expanded), the interior wall forming the cavity of the patient 102, and the main body 130) may be operable to provide, or contribute in providing, the expanding of one or more of the expandable members 122, 124. For example, as the gas in the region between the first expandable member 122 (when expanded), the second expandable member 124 (when expanded), the interior wall forming the cavity of the patient 102, and the main body 130 is being suctioned or removed, the said suctioned or removed gas may be provided into one or more of the expandable members 122, 124. In such an example, a filter, or the like, may be provided to remove unwanted particles, liquid, and/or gas from entering and/or exiting the expandable members 122, 124.

It is to be understood in the present disclosure that, in example embodiments wherein the anchor assembly 120 comprises more than two expandable members, the suction openings 126 may be provided between some or all of the expandable members. For example, if the anchor assembly 120 comprises three expandable members, then suction openings 126 may be provided between each of the three expandable members.

Each expandable member 122, 124, and cross-section thereof, may be formed in any one of a plurality of shapes, sizes, and/or dimensions. For example, the expandable members 122, 124 may resemble a tablet or donut shape with a circular cross-section. A cross sectional shape of the expandable members 122, 124 may also be one or more of a rectangle, square, pentagon, hexagon, etc., or combination of one or more geometric shapes, without departing from the teachings of the present disclosure.

In an example embodiment wherein the cross-sectional shape of the expandable members 122, 124 is circular, an outer diameter of the expandable members 122, 124 may be between about 3 to 100 mm. The distance that the expandable members 122, 124 may be expanded radially away from and contracted towards the main body 130 may be between about 0.05 to 50 mm. It is to be understood in the present disclosure that the above dimensions are merely an illustration of example embodiments, and as such the dimensions may be smaller or larger than those recited above without departing from the teachings of the present disclosure.

The expandable members 122, 124 may be formed using any one or more of a plurality of materials, such as surgical-grade plastics, rubbers, etc. It is to be understood in the present disclosure that the material forming the surface pattern, roughness, and/or protrusion of the surface of the expandable members 122, 124 may be the same as, or different from, the material of the rest of the expandable members 122, 124. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Second Main Body (e.g., Second Main Body 150)

FIG. 1, FIGS. 2B-C, FIGS. 3A-G, and FIG. 3I illustrate an example embodiment of the second main body 150 of the endoscopic system 100. As used in the present disclosure, the second main body 150 may also be referred to as the outer body 150, second tube 150, outer tube 150, and/or the like. The second main body 150 may comprise a first end 150a and an exposed end portion 150b.

A portion of the main body 130 near the first end 150a may, or may not, be selectively configurable to actuate (and/or bend, turn, pivot, twist, move, and/or the like) in one or more of a plurality of directions (and/or positions, locations, and/or the like) with respect to the other portions of the second main body 150. Such actuating of a portion of the second main body 150 may be similar to, the same as, based on, or different from the actuating described above for the main body 130. The second main body 150 may be selectively configured and/or controlled to slide, that is, extend outwardly and/or retract inwardly, with respect to the main body 130 in example embodiments, as illustrated in FIG. 3C. It is recognized in the present disclosure that sliding and/or actuating of at least a portion of the second main body 150 with respect to the main body 130 may enable the endoscopic system 100 to advance around flexural and/or looping/bending sections of the cavity, such as the colonic lumen, of the patient without forceful manual pushing against the interior wall forming the cavity of the patient.

Figure 3I:
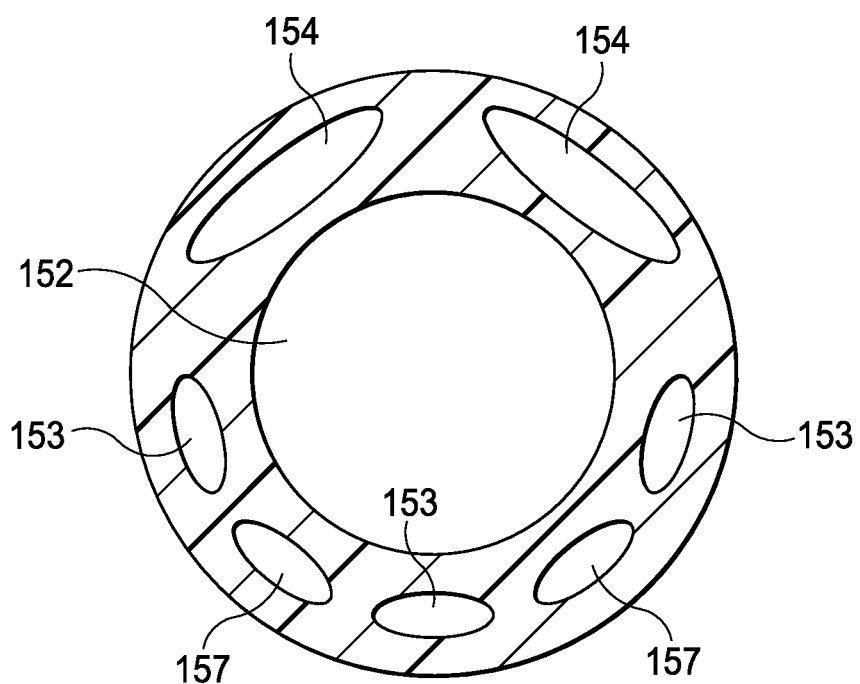
FIG. 3I is an illustration of a cross-sectional view of an example embodiment of the second main body.

In an example embodiment illustrated in FIG. 3I, the second main body 150 may comprise one or more movement control cavities 153, or the like. Each movement control cavity 153 may be operable to receive and/or house a filler, and/or the like. The filler may be any substance or material, including a gas, such as air, carbon dioxide, nitrogen, a liquid, such as water, oil, and/or a solid, such as micro particle. When it is desired to actuate a movement, control, and/or position of a portion of the second main body 150, such as the portion of the second main body 150 closer to the first end 150a, in a specific desired direction and/or position, a predetermined selection and/or combination of one or more of the movement control cavities 153 may be selectively configured and controlled. For example, one or more of the movement control cavities 153 may house one or more types of fillers, such as a gas, and such fillers may be manipulated, manually by operator/surgeon and/or via controller 160, to actuate the portion of the second main body 150, such as via the pressure control subsystem 170, expansion source subsystem 194, etc. As another example, one or more of the movement control cavities 153 may be provided with a predetermined quantity of one or more types of fillers when actuating of the portion of the second main body 150 is required. As another example, the properties of the filler material housed in one or more of the movement control cavities 153 may be selectively configured to change, such as change in volume (expand and/or contract), stiffen, become more flexible, change from gas to liquid phase (and vice versa), change from liquid to solid phase (and vice versa), change from gas to solid phase (and vice versa), change in pressure, change in temperature, change in shape/size, change in tensile strength, etc. To effect one or more such changes, the one or more fillers may be a material (or combination of materials) selected in such a way that an introduction, application, change, and/or removal of an application, each as applicable, of an electric current, voltage potential, resistance, pressure, temperature, magnetic field, and/or the like, causes one or more of the above-mentioned changes in properties. For example, the filler may be a memory-shaped metal, other material, spring-based or spring-like material, or the like.

In example embodiments, the actuating of the second main body 150, including the portion of the second main body 150 closer to the first end 150a, as described above and in the present disclosure, may be performed and/or controlled by the controller 160 and/or an operator/surgeon, either manually and/or via the controller 160. Furthermore, the amount of filler, change in quantity of filler, and/or change in properties of the filler in the one or more movement control cavities 153 may be stored in the computer-readable medium 162.

It is to be understood in the present disclosure that other elements and/or methods for actuating a movement, control, and/or position of a portion of the second main body 150 and/or other elements of the endoscopic system 100 are contemplated without departing from the teachings of the present disclosure.

As illustrated in at least FIG. 3I, in example embodiments, the second main body 150 may further comprise one or more main cavities 152. The main cavity 152 may be operable to enable the main body 130 to move with respect to the second main body 150, and vice versa. Other main cavities 152 may be provided in example embodiments having other main bodies, such as one or more intermediate bodies (not shown) between or adjacent to the main body 130 and the second main body 130. Furthermore, other main cavities 152 may be provided in example embodiments having one or more head assemblies 110', as illustrated in FIG. 2B.

In example embodiments, the second main body 150 may further comprise one or more instrument cavities (not shown). Such instrument cavities of the second main body 150 may be operable to enable instruments, such as instrument 112 and/or other instruments (not shown), to move with respect to the second main body 150, and/or enable cables (if any) and/or connections (if any) of such instruments to be accessible by the operator/surgeon and/or connected to the controller 160 and/or computer-readable medium 162. For example, such instrument cavities of the second main body 150 may be operable to enable an instrument to perform a therapeutic/surgical procedure on a portion of an interior wall forming the cavity of the patient that is between the first anchor assembly 120 and the second anchor assembly 140.

The second main body 150 may further comprise one or more irrigation cavities (not shown). Such irrigation cavity of the second main body 150 may be operable to enable the movement of liquid and/or solids into and/or out of the cavity of the patient. Such irrigation cavity of the second main body 150 may be connected to the irrigation cavity 114, 134 and/or other irrigation cavities and/or openings (not shown). Furthermore, such irrigation cavity of the second main body 150 may also be connected to the irrigation subsystem 190 in example embodiments. In an example embodiment, such irrigation cavity of the second main body 150 may be operable to enable movement of liquid and/or solids into and/or out of the cavity of the patient in an region that is between the first anchor assembly 120 and the second anchor assembly 140.

In example embodiments, the second main body 150 may further comprise one or more insufflation/suction cavities (not shown). Such insufflation/suction cavity of the second main body 150 may be operable to provide and/or remove a gas (i.e., provide a positive pressure and/or a negative pressure, respectively) for use in performing insufflation or suction of the cavity of the patient. Such insufflation/suction cavity of the second main body 150 may or may not be connected to the insufflation cavity 115, 135. Furthermore, such insufflation/suction cavity of the second main body 150 may also be connected to the insufflation subsystem 192, pressure control subsystem, and/or a different subsystem in example embodiments. In an example embodiment, such insufflation/suction cavity of the second main body 150 may be operable to provide insufflation and/or suction in an region that is between the first anchor assembly 120 and the second anchor assembly 140.

As illustrated in at least FIG. 3I, in example embodiments, the second main body 150 may further comprise one or more anchor cavities 154 operable to configure, control, and/or assist in configuring and/or controlling the second anchor assembly 140. The anchor cavity 154 may be operable to provide a gas, liquid, and/or solid, and/or combination thereof, for use in expanding (such as expanding radially from the main body 130) one or more of the third expandable member 142 and the fourth expandable member 144. The anchor cavity 154 may be connected to one or more of the third expandable member 142 and the fourth expandable member 144. The anchor cavity 154 may also be connected to an expansion source subsystem 194 in example embodiments. The second anchor assembly 140 will be further described below.

As illustrated in at least FIG. 3H, in example embodiments, the second main body 150 may further comprise one or more suction cavities 157. The suction cavity 157 may be operable to provide a negative pressure (or perform a removal of gas). For example, the suction cavity 157 may be operable to apply a negative pressure to a region between the third expandable member 142 (when expanded), the fourth expandable member 144 (when expanded), the interior wall forming the cavity of the patient 102, and the second main body 150. The suction cavity 157 may be connected to the suction opening 146. The suction cavity 157 may also be connected to the pressure control subsystem 170 in example embodiments. The suction opening 146 will be further described below.

It is to be understood in the present disclosure that the second main body 150, including one or more of the instrument cavities (not shown), movement control cavities 153, irrigation cavity (not shown), irrigation subsystem 190, insufflation/suction cavity (not shown), insufflation subsystem 192, anchor cavities 154, expansion source subsystem 194, suction cavities 157, and pressure control subsystem 170 may be provided in a configuration that is the same as, similar to, based on, or different from that illustrated in the example embodiment of FIG. 3I without departing from the teachings of the present disclosure. Furthermore, one or more of the instrument cavities (not shown), movement control cavities 153, irrigation cavity (not shown), irrigation subsystem 190, insufflation/suction cavity (not shown), insufflation subsystem 192, anchor cavities 154, expansion source subsystem 194, suction cavities 157, and pressure control subsystem 170 may be provided, or not provided, in the second main body 150 without departing from the teachings of the present disclosure.

The second main body 150, and cross-section thereof, may be formed in any one of a plurality of shapes, sizes, and/or dimensions. For example, the second main body 150 may be an elongated cylindrical body, as illustrated in FIGS. 1 to 3. A cross sectional shape of the second main body 150 may also be one or more of a rectangle, square, pentagon, hexagon, etc., or combination of one or more geometric shapes, without departing from the teachings of the present disclosure.

In an example embodiment wherein the cross-sectional shape of the second main body 150 is cylindrical in shape with a circular cross-section, an outer diameter of the second main body 150 may be between about 6 to 35 mm. The length of the second main body 150 may be expanded/contracted between about 50 to 200 cm. It is to be understood in the present disclosure that the above dimensions are merely an illustration of example embodiments, and as such the dimensions may be smaller or larger than those recited above without departing from the teachings of the present disclosure.

The second main body 150 may be formed using any one or more of a plurality of materials, such as surgical-grade plastics, rubbers, etc. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Second Anchor Assembly (e.g., Second Anchor Assembly 140)

A perspective view of an example embodiment of an expanded second anchor assembly 140 (e.g., second anchor assembly 140 expanded radially from the second main body 150) is illustrated in at least FIG. 1; a side view of an example embodiment of an expanded second anchor assembly 140 (e.g., second anchor assembly 140 expanded radially from the second main body 150) is illustrated in at least FIGS. 2B-C, FIG. 3A, FIGS. 3D-E, and FIG. 3G; and a side view of an example embodiment of an un-expanded second anchor assembly 140 (e.g., second anchor assembly 140 not expanded radially from the second main body 150) is illustrated in at least FIGS. 3B-C. The second anchor assembly 140 may be attachable to the second main body 150. During diagnostic and/or therapeutic/surgical procedures, the second anchor assembly 140 may be fixedly attached to the second main body 150 near the first end 150a of the second main body 150.

The second anchor assembly 140 may be configurable to perform, among other things, a securing of a position and/or location of the second main body 150. In an example embodiment, when the endoscopic system 100 is inserted into the cavity of the patient, as illustrated in at least FIG. 2C, FIGS. 3D-E, and FIG. 3G, the second anchor assembly 140 may be configurable to secure the second main body 150 with respect to the interior wall forming the cavity of the patient. The second anchor assembly 140 may secure the second main body 150 with respect to the interior wall forming the cavity of the patient in one or more of a plurality of ways. In an example embodiment, one or more expandable members 142, 144 may be expanded to contact the interior walls forming the cavity of the patient. The second anchor assembly 140 may also secure the second main body 150 with respect to the interior wall forming the cavity of the patient by applying a negative pressure via one or more second suction openings 146. The second anchor assembly 140 may also secure the second main body 150 with respect to the interior wall forming the cavity of the patient via one or more surface patterns, roughness, protrusions, and/or the like formed on a surface, or portion(s) thereof, of one or more expandable members 142, 144. The second anchor assembly 140 may also secure the second main body 150 with respect to the interior wall forming the cavity of the patient using a magnetic element and corresponding external magnetic element provided outside of the patient. The securing, by the second anchor assembly 140, of the second main body 150 with respect to the interior wall forming the cavity of the patient will now be further described below.

The second anchor assembly 140 may comprise one or more expandable members 142, 144. During diagnostic and/or therapeutic/surgical procedures, the one or more expandable members 142, 144 may be fixedly attached to the second main body 150 near the first end 150a of the second main body 150. In an example embodiment, the second anchor assembly 140 may comprise third expandable member 142. As used in the present disclosure, the third expandable member 142 may also be referred to as the expandable member 142, third balloon 142, and/or the like. The second anchor assembly 140 may further comprise fourth expandable member 144. The fourth expandable member 144 may be provided between the third expandable member 142 and the first end 150a of the second main body 150. As used in the present disclosure, the fourth expandable member 144 may also be referred to as the expandable member 144, fourth balloon 144, and/or the like. It is to be understood in the present disclosure that the second anchor assembly 140 may comprise other quantities of expandable members, such as one or more additional expandable members, without departing from the teachings of the present disclosure.

Each expandable member 142, 144 may be configurable to change its volume/size to be a minimum volume/size, a maximum volume/size, and a volume/size between the minimum and maximum volumes/sizes. For example, each expandable member 142, 144 may be configurable to expand radially away from the second main body 150.

In an example embodiment, each expandable member 142, 144 may be a hollow member resembling a balloon, or the like. In this regard, each expandable member 142, 144 may be operable to expand (i.e., secure the second main body 150) by receiving a gas (or positive pressure), liquid, solid, and/or combination thereof. The expanding of the expandable member 142, 144 may occur partially, substantially, or completely in a direction away from the second main body 150 (i.e., radially away from the second main body 150). Furthermore, each expandable member 142, 144 may be operable to reduce in size (or contract or un-secure the main body 130) by removing the gas (or removing the positive pressure or applying a negative pressure), liquid, solid, and/or combination thereof, received in the expandable member 142, 144. To secure the second main body 150 with respect to the interior wall forming the cavity of the patient, the one or more expandable members 142, 144 may be expanded to contact the interior wall forming the cavity of the patient. It is recognized in the present disclosure that the expanding and contacting of the one or more expandable members 142, 144 with the interior wall forming the cavity, such as the colonic lumen, of the patient may provide for a sufficient securing or anchoring of the second main body 150 so as to withstand a force of at least 0.1 to 20 N.

One or more of the expandable members 142, 144 may comprise one or more surface patterns, roughness, protrusions, and/or the like formed on a surface, or portion(s) thereof, of the one or more expandable members 142, 144. During diagnostic and/or therapeutic/surgical procedures wherein a securing or anchoring of the second main body 150 with respect to the interior wall forming the cavity of the patient is desired or required, such surface patterns, roughness, protrusions, and/or the like formed on the surface of one or more expandable members 142, 144 that are in contact with the interior wall forming the cavity of the patient may further improve the securing or anchoring of the second main body 150. For example, the surface pattern, roughness, protrusions, and/or the like may provide, or contribute in providing, resistance of a movement of one or more of the expandable members 142, 144 contacting the interior wall forming the cavity of the patient with respect to the interior wall forming the cavity of the patient. It is recognized in the present disclosure that such securing or anchoring of the second main body 150 may be operable to withstand a force of at least 0.10 to 30 N.

It is to be understood in the present disclosure that the second anchor assembly 140, including one or more of the third and fourth expandable members 142, 144, may or may not be a hollow member resembling a balloon, tire, or the like. For example, one or more of the third and fourth expandable members 142, 144 may only be partially hollow. As another example, one or more of the third and fourth expandable members 142, 144 may be formed partially, substantially, and/or entirely of an expandable solid and/or liquid. In this regard, the properties of such material forming one or more of the third and fourth expandable members 142, 144 may be selectively configured to change, such as change in volume (expand and/or contract), stiffen, become more flexible, change from gas to liquid phase (and vice versa), change from liquid to solid phase (and vice versa), change from gas to solid phase (and vice versa), change in pressure, change in temperature, change in shape, change in size, change in tensile strength, etc. To effect one or more such changes, such material forming one or more of the third and fourth expandable members 142, 144 may be a material (or combination of materials) selected in such a way that an introduction, application, change, and/or removal of an application, each as applicable, of an electric current, voltage potential, resistance, pressure, temperature, magnetic field, and/or the like, causes one or more of the above-mentioned changes in properties. For example, such material may be a memory-shaped metal, other material, spring-based or spring-like material, or the like.

In some example embodiments, the second anchor assembly 140 may comprise one or more expandable members that expand radially away from the second main body 150 and in other directions, such as the example illustrated in FIG. 4B. In other example embodiments, such as the example illustrated in FIG. 4A, the second anchor assembly 140 may comprise an integrated third and fourth expandable members 142, 144, or the like. In other example embodiments, such as the example illustrated in FIG. 4C, the second anchor assembly 140 may comprise a magnetic element 146', or the like, operable to secure to a corresponding magnetic element provided outside of the patient.

The second anchor assembly 140 may further comprise one or more second suction openings 146. As used in the present disclosure, the second suction opening 146 may also be referred to as the suction opening 146. The second suction opening 146 may be formed in one or more of a plurality of shapes and provided in one or more quantities. FIG. 4D illustrates example embodiments of the one or more second suction openings 146. During diagnostic and/or therapeutic/surgical procedures wherein a securing or anchoring of the second main body 150 with respect to the interior wall forming the cavity of the patient is desired or required, the one or more second suction openings 146 may further improve the securing or anchoring of the second main body 150. For example, the second suction opening 146 may be operable to apply a negative pressure to a region between the third expandable member 142 (when expanded), the fourth expandable member 144 (when expanded), the interior wall forming the cavity of the patient 104 (as illustrated in at least FIG. 3E), and the second main body 150. In example embodiments, the second suction opening 146 may be configurable to apply a negative pressure and vary the applied negative pressure between about −10 kPa to vacuum. It is recognized in the present disclosure that such securing or anchoring of the second main body 150 with the use of the expanded third and fourth expandable members 142, 144 and the one or more second suction openings 146 may provide improved securing or anchoring, and may be operable to withstand a force of at least 0.1 to 40 N.

In example embodiments, the applying of the negative pressure by the second suction opening 146 (i.e., the suctioning or removal of gas from the region between the third expandable member 142 (when expanded), the fourth expandable member 144 (when expanded), the interior wall forming the cavity of the patient 104, and the second main body 150) may be performed prior to, at the same time as (or correspond with), and/or after the expansion of the expandable members 142, 144. Furthermore, in example embodiments, the applying of the negative pressure by the second suction opening 146 (i.e., the suctioning or removal of gas from the region between the third expandable member 142 (when expanded), the fourth expandable member 144 (when expanded), the interior wall forming the cavity of the patient 104, and the second main body 150) may be operable to provide, or contribute in providing, the expanding of one or more of the expandable members 142, 144. For example, as the gas in the region between the third expandable member 142 (when expanded), the fourth expandable member 144 (when expanded), the interior wall forming the cavity of the patient 104, and the second main body 150 is being suctioned or removed, the said suctioned or removed gas may be provided into one or more of the expandable members 142, 144. In such an example, a filter, or the like, may be provided to remove unwanted particles, fluid, and/or gas from entering and/or exiting the expandable members 142, 144.

It is to be understood in the present disclosure that, in example embodiments wherein the second anchor assembly 140 comprises more than two expandable members, the second suction openings 146 may be provided between some or all of the expandable members. For example, if the second anchor assembly 140 comprises three expandable members, then second suction openings 146 may be provided between each of the three expandable members.

Each expandable member 142, 144, and cross-section thereof, may be formed in any one of a plurality of shapes, sizes, and/or dimensions. For example, the expandable members 142, 144 may resemble a tablet or donut shape with a circular cross-section. A cross sectional shape of the expandable members 142, 144 may also be one or more of a rectangle, square, pentagon, hexagon, etc., or combination of one or more geometric shapes, without departing from the teachings of the present disclosure.

In an example embodiment wherein the cross-sectional shape of the expandable members 142, 144 is circular, an outer diameter of the expandable members 142, 144 may be between about 5 to 100 mm. The distance that the expandable members 142, 144 may be expanded radially away from and contracted towards the second main body 150 may be between about 0.05 to 50 mm. It is to be understood in the present disclosure that the above dimensions are merely an illustration of example embodiments, and as such the dimensions may be smaller or larger than those recited above without departing from the teachings of the present disclosure.

The expandable members 142, 144 may be formed using any one or more of a plurality of materials, such as surgical-grade plastics, rubbers, etc. It is to be understood in the present disclosure that the material forming the surface pattern, roughness, and/or protrusion of the surface of the expandable members 142, 144 may be the same as, or different from, the material of the rest of the expandable member 142, 144. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Controller (e.g., Controller 160)

Figure 6:
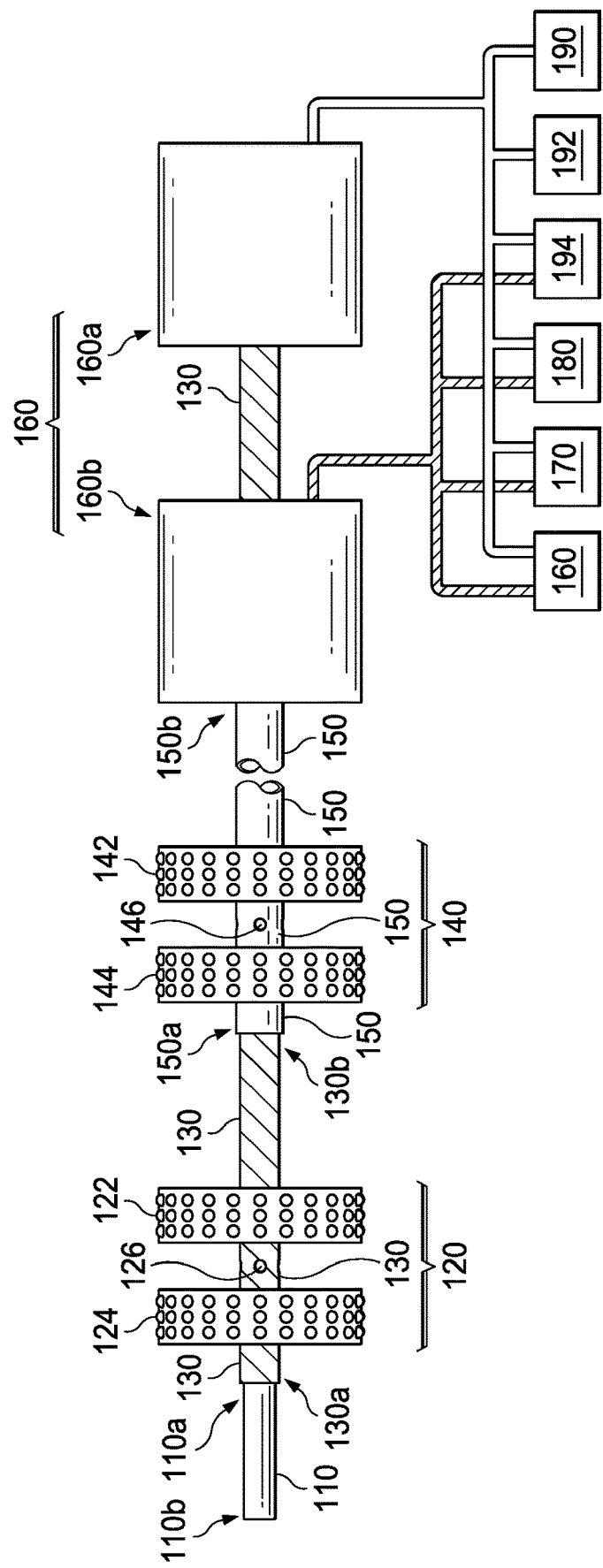
FIG. 6 is an illustration of an example embodiment of the endoscopic system having an example embodiment of a controller.
Figure 7A:
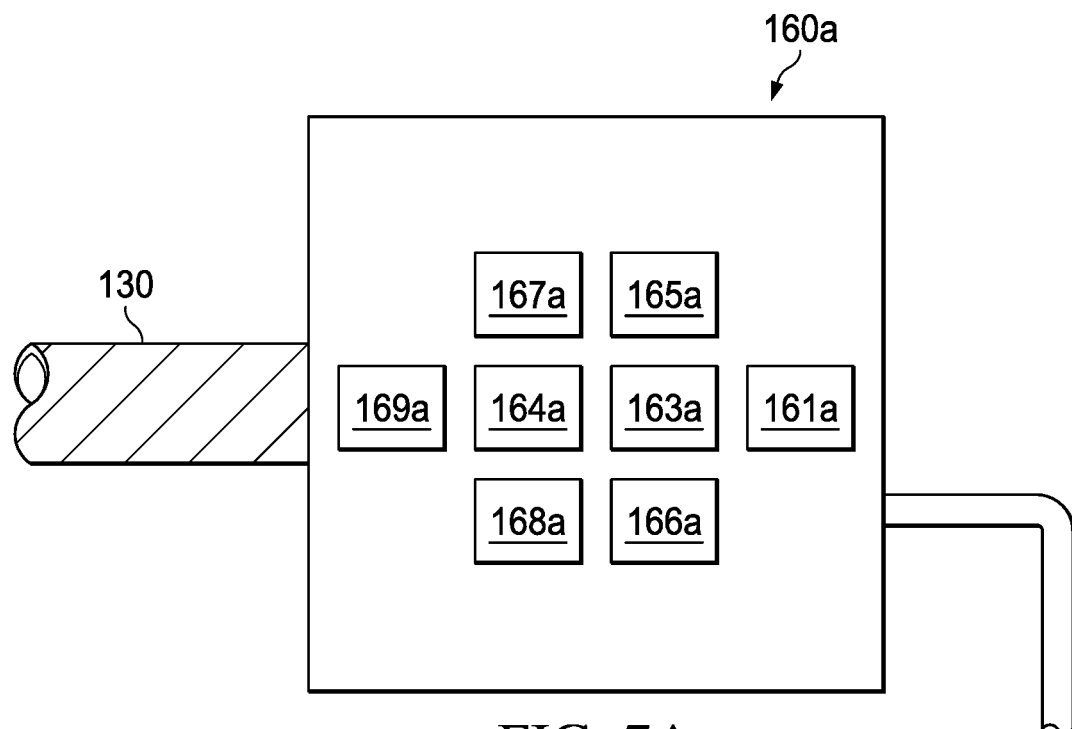
FIG. 7A is an illustration of an example embodiment of a first controller.
Figure 7B:
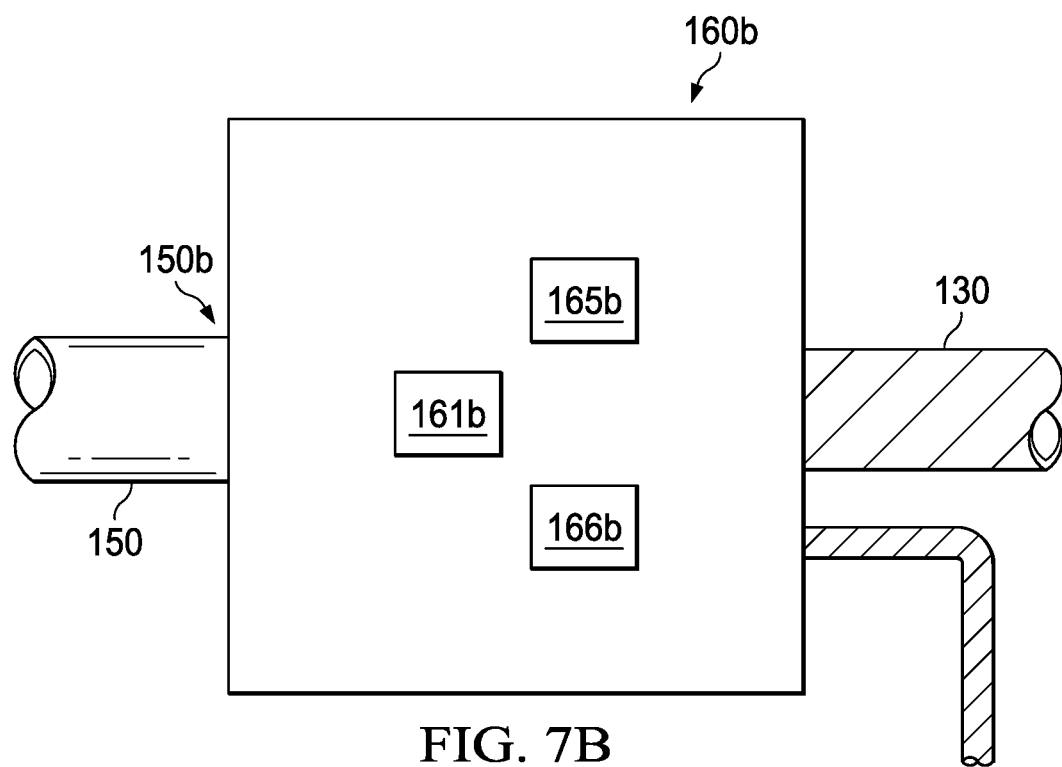
FIG. 7B is an illustration of an example embodiment of a second controller.

As illustrated in at least FIG. 6, FIG. 7A, and FIG. 7B, an example embodiment of the endoscopic device 100 may include a controller system (e.g., controller 160). The controller 160 may be provided and configured in one or more of a plurality of ways. For example, the controller 160 may be housed, in whole or in part, in one or more portions of the endoscopic system 100, such as the head assembly 110, main body 130, and/or second main body 150, and/or provided at second end 150b. The controller 160 may comprise logic stored in non-transitory computer readable medium which, when executed by a processor associated or in communication with the controller 160, may be operable to perform one or more actions, operations, configurations, and/or communications (such as monitoring and/or controlling) with one or more elements of the endoscopic device 100. The controller 160 may also be operable to, wirelessly or via wires, receive commands and/or interactions from an operator (such as a surgeon) and respond by performing said one or more actions, operations, configurations, and/or communications with one or more elements of the endoscopic device 100.

The controller 160 may be any apparatus, device, processor, or the like, or combination thereof, operable to communicate (including monitor and/or control), wirelessly or via wires, with one or more elements of endoscopic system 100 including, but not limited to, the head assembly 110, first end portion 110a, second end portion 110b, image capturing assembly 111, instrument assembly 112, movement control cavity 113, irrigation cavity 114, insufflation cavity 115, first anchor assembly 120, second expandable member 122, first expandable member 124, first suction opening 126, main body 130, first end 130a, second end 130b, movement control cavity 133, irrigation cavity 134, insufflation cavity 135, anchor cavities 136, suction cavity 137, second anchor assembly 140, fourth expandable member 142, third expandable member 144, second suction opening 146, second main body 150, first end 150a, second end 150b, main cavity 152, movement control cavity 153, anchor cavities 154, suction cavity 157, pressure control subsystem 170, power source 180, irrigation subsystem 190, insufflation subsystem 192, expansion source subsystem 194, and/or other processors, computing devices, and/or controllers (not shown).

As illustrated in FIGS. 6, 7A, and 7B, an example embodiment of the controller 160 may comprise a first controller (e.g., main body controller) 160a for use in performing one or more actions, operations, configurations, and/or communications with those elements of and/or associated with the first main body 130 and a second controller (e.g., second main body controller) 160b for use in performing one or more actions, operations, configurations, and/or communications with those elements of and/or associated with the second main body 150. Although the figures may illustrate the controller 160 comprising first controller 160a and second controller 160b, it is to be understood in the present disclosure that the controller 160 may comprise more or less subsystems without departing from the teachings of the present disclosure. It is also to be understood in the present disclosure that the actions, operations, configurations, and/or communications of the first controller 160a need not be limited to only those elements of and/or associated with the first main body 130. For example, the first controller 160a may also be for use in performing actions, operations, configurations, and/or communications with elements of and/or associated with the second main body 150 in example embodiments. Likewise, it is to be understood in the present disclosure that the actions, operations, configurations, and/or communications of the second controller 160a need not be limited to only those elements of and/or associated with the second main body 150. For example, the second controller 160b may also be for use in performing actions, operations, configurations, and/or communications with elements of and/or associated with the first main body 130 in example embodiments.

The First Controller (e.g., First Controller 160a)

In an example embodiment, the first controller 160a may be operable to control, either through automatic control by a processor and/or manual control by an operator, a forward movement of the first main body 130. For example, the first controller 160a and/or an element (e.g., 161a) associated with the first controller 160a (such as a button, joystick, thumbstick, touchpad, motion control, voice control, accelerometer, haptic feedback, or the like, or physical elements such as an external body, gripping portion, etc. of the first controller 160a) may be interacted with so as to advance the first main body 130 forward relative to (or away from) the second controller 160b (and/or second main body 150 and/or external body, gripping portion, etc. of the second controller 160b). In this regard, the second controller 160b (and/or second main body 150 and/or external body, gripping portion, etc. of the second controller 160b) may be secured and/or anchored in place (such as via second anchor assembly 140, an anchoring tool (not shown), and/or an operator) relative to the patient (and/or surgical bed) so as to enable the first main body 130 to be advanced inward/forward.

In an example embodiment, the first controller 160a may also be operable to control, either through automatic control by a processor and/or manual control by an operator, a backward movement of the first main body 130. For example, the first controller 160*a* and/or an element (e.g., 161*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) may be interacted with so as to move the first main body 130 towards the second main body 150. In this regard, the second controller 160*b* (and/or second main body 150 and/or external body, gripping portion, etc. of the second controller 160*b*) may be secured and/or anchored in place (such as via second anchor assembly 140, an anchoring tool (not shown), and/or an operator) relative to the patient (and/or surgical bed).

In an example embodiment, the first controller 160*a* may also be operable to control, either through automatic control by a processor and/or manual control by an operator, an actuating (such as a bending, straightening, turning, pivoting, twisting, moving, etc.) of the first main body 130 (such as a bending, straightening, turning, pivoting, twisting, moving, etc. of the first end portion 130*a*) in one or more of a plurality of directions. For example, the first controller 160*a* and/or an element (e.g., 161*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) may be controlled by an operator so as to enable the first main body 130 to actuate as desired by the operator. In this regard, the pressure control subsystem 170, expansion source subsystem 194, and/or the like, associated with or connected to the one or more movement control cavities 133 of the first main body 130, as described above and in the present disclosure, may be controllable by the first controller 160*a* and/or an element (e.g., 161*a*) associated with the first controller 160*a* (such as buttons, joysticks, thumbsticks, touchpad, or the like of the first controller 160*a*) so as to enable the first main body 130 to actuate as desired.

In an example embodiment, the first controller 160*a* may also be operable to control, either through automatic control by a processor and/or manual control by an operator, an expanding and/or contracting of the first anchor assembly 120. For example, the first controller 160*a* and/or an element (e.g., 165*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) may be controlled by an operator so as to enable the first anchor assembly 120 to expand and/or contract as desired by the operator. In this regard, expansion source subsystem 194, and/or the like, associated with or connected to the first anchor assembly 120 of the first main body 130, as described above and in the present disclosure, may be controllable by the first controller 160*a* and/or an element (e.g., 165*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) so as to enable the first anchor assembly 120 to expand and/or contract as desired.

In an example embodiment, the first controller 160*a* may also be operable to control, either through automatic control by a processor and/or manual control by an operator, an expanding and/or contracting of one or more of the second expandable member 122 and first expandable member 124. For example, the first controller 160*a* and/or an element (e.g., 165*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) may be controlled by an operator so as to enable one or more of the second expandable member 122 and first expandable member 124 to expand and/or contract as desired by the operator. In this regard, expansion source subsystem 194, and/or the like, associated with or connected to one or more of the second expandable member 122 and first expandable member 124, as described above and in the present disclosure, may be controllable by the first controller 160*a* and/or an element (e.g., 165*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) so as to enable one or more of the second expandable member 122 and first expandable member 124 to expand and/or contract as desired.

In an example embodiment, the first controller 160*a* may also be operable to control, either through automatic control by a processor and/or manual control by an operator, an applying and/or not applying of a suctioning (or applying negative pressure) via first suction opening(s) 126. For example, the first controller 160*a* and/or an element (e.g., 166*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) may be controlled by an operator so as to enable the first suction opening(s) 126 to apply a suction (or negative pressure) and/or not apply a suction (no pressure or positive pressure) as desired by the operator. In this regard, pressure control subsystem 170, and/or the like, associated with or connected to the first suction opening(s) 126 of the first main body 130, as described above and in the present disclosure, may be controllable by the first controller 160*a* and/or an element (e.g., 166*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) so as to enable the first suction opening(s) 126 to apply and/or not apply suction as desired. It is to be understood in the present disclosure that the first controller 160*a* may be operable to control the expanding and contracting of the first anchor assembly 120 (and/or each of the first and second expandable members 124, 122) at the same time as the applying and not applying of the suctioning by the first suction opening(s) 126, respectively (e.g., using a single control, interaction, action, and/or command to perform both). For example, when the first anchor assembly 120 is controlled to expand, the first suction opening(s) 126 may be controlled to apply a suction. Similarly, when the first anchor assembly 120 is controlled to contract, the first suction opening(s) 126 may be controlled to not apply a suction.

In an example embodiment, the first controller 160*a* may also be operable to control, either through automatic control by a processor and/or manual control by an operator, a forward movement of the head assembly 110. For example, the first controller 160*a* and/or an element (e.g., 163*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) may be interacted with so as to advance the head assembly 110 forward relative to the first main body 130. In this regard, the first main body 130 may be secured and/or anchored in place (such as via first anchor assembly 120, second anchor assembly 140, an anchoring tool (not shown), and/or an operator) relative to the patient (and/or surgical bed) so as to enable the head assembly 110 to be advanced forward.

In an example embodiment, the first controller 160*a* may also be operable to control, either through automatic control by a processor and/or manual control by an operator, a backward movement of the head assembly 110. For example, the first controller 160*a* and/or an element (e.g., 163*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) may be interacted with so as to move the head assembly 110 backwardly (i.e., towards the first main body 130). In this regard, the first main body 130 may be secured and/or anchored in place (such as via first anchor assembly 120, second anchor assembly 140, an anchoring tool (not shown), and/or an operator) relative to the patient (and/or surgical bed) so as to enable the head assembly 110 to be pulled backwardly (i.e., towards the first main body 130).

In an example embodiment, the first controller 160*a* may also be operable to control, either through automatic control by a processor and/or manual control by an operator, an actuating (such as a bending, straightening, turning, pivoting, twisting, moving, etc.) of the head assembly 110 (such as a bending, straightening, turning, pivoting, twisting, moving, etc. of the second end portion 110*b*) in one or more of a plurality of directions. For example, the first controller 160*a* and/or an element (e.g., 163*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) may be controlled by an operator so as to enable the head assembly 110 to actuate as desired by the operator. In this regard, the pressure control subsystem 170, expansion source subsystem 194, and/or the like, associated with or connected to the one or more movement control cavities 113 of the head assembly 110, as described above and in the present disclosure, may be controllable by the first controller 160*a* and/or an element (e.g., 163*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) so as to enable the head assembly 110 to actuate as desired.

In an example embodiment, the first controller 160*a* may also be operable to control, either through automatic control by a processor and/or manual control by an operator, a forward movement of the instrument assembly 112. For example, the first controller 160*a* and/or an element (e.g., 164*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) may be interacted with so as to advance the instrument assembly 112 away from the head assembly 110 (such as via the instrument cavity 131). In this regard, the head assembly 110 may be secured and/or anchored in place (such as via first anchor assembly 120, second anchor assembly 140, an anchoring tool (not shown), and/or an operator) relative to the patient (and/or surgical bed) so as to enable the instrument assembly 112 to be advanced forward.

In an example embodiment, the first controller 160*a* may also be operable to control, either through automatic control by a processor and/or manual control by an operator, a backward movement of the instrument assembly 112. For example, the first controller 160*a* and/or an element (e.g., 164*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) may be interacted with so as to move the instrument assembly 112 (i.e., towards the head assembly 110). In this regard, the head assembly 110 may be secured and/or anchored in place (such as via first anchor assembly 120, second anchor assembly 140, an anchoring tool (not shown), and/or an operator) relative to the patient (and/or surgical bed) so as to enable the instrument assembly 112 to be pulled backwardly (i.e., towards the head assembly 110).

In an example embodiment, the first controller 160*a* may also be operable to control, either through automatic control by a processor and/or manual control by an operator, an operating the instrument assembly 112 (such as performing a cutting and/or gripping action when in operation). For example, the first controller 160*a* and/or an element (e.g., 164*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) may be interacted with so as to perform an action (such as a cutting, gripping, etc.) using the instrument assembly 112 (such as via the instrument cavity 131).

In an example embodiment, the first controller 160*a* may also be operable to control, either through automatic control by a processor and/or manual control by an operator, a recording, image capturing, zooming, and/or panning operations of the image capturing assembly 111. For example, the first controller 160*a* and/or an element (e.g., 169*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) may be interacted with so as to perform an action (such as a recording, image capturing, zooming, panning, illuminating, etc.) using the image capturing assembly 111 via the image capturing cavity 131.

In an example embodiment, the first controller 160*a* may also be operable to control, either through automatic control by a processor and/or manual control by an operator, an enabling movement of solids and/or liquids by the irrigation cavity 134. For example, the first controller 160*a* and/or an element (e.g., 168*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) may be interacted with so as to enable a movement of solids and/or liquids using the irrigation cavity 134 via the irrigation cavity 114 and irrigation system 190.

In an example embodiment, the first controller 160*a* may be operable to control, either through automatic control by a processor and/or manual control by an operator, an enabling insufflation by the insufflation cavity 135. For example, the first controller 160*a* and/or an element (e.g., 167*a*) associated with the first controller 160*a* (such as a button, joystick, thumbstick, touchpad, motion control, voice control, accelerometer, haptic feedback, or the like, or physical elements such as an external body, gripping portion, etc. of the first controller 160*a*) may be interacted with so as to enable an insufflation of a cavity of the patient using the insufflation cavity 135 via the insufflation cavity 115 and insufflation system 192.

The Second Controller (e.g., Second Controller 160*b*)

In respect to the second controller 160*b*, in an example embodiment, the second controller 160*b* may be operable to control, either through automatic control by a processor and/or manual control by an operator, a forward movement of the second main body 150. For example, the second controller 160*b* and/or an element (e.g., 161*b*) associated with the second controller 160*b* (such as a button, joystick, thumbstick, touchpad, motion control, voice control, accelerometer, haptic feedback, or the like, or physical elements such as an external body, gripping portion, etc. of the second controller 160*b*) may be interacted with so as to advance the second main body 150 forward relative to (or towards) the first controller 160*a* (and/or first main body 130 and/or external body, gripping portion, etc. of the first controller 160*a*). In this regard, the first controller 160*a* (and/or first main body 130 and/or external body, gripping portion, etc. of the first controller 160*a*) may be secured and/or anchored in place (such as via first anchor assembly 120, an anchoring tool (not shown), and/or an operator) relative to the patient (and/or surgical bed) so as to enable the second main body 150 to be advanced inward/forward.

In an example embodiment, the second controller 160*b* may be operable to control, either through automatic control by a processor and/or manual control by an operator, a backward movement of the second main body 150. For example, the second controller 160*b* and/or an element (e.g., 161*b*) associated with the second controller 160*b* (such as a button, joystick, thumbstick, touchpad, motion control, voice control, accelerometer, haptic feedback, or the like, or physical elements such as an external body, gripping portion, etc. of the second controller 160*b*) may be interacted with so as to move the second main body 150 away from the first main body 130. In this regard, the first controller 160*a* (and/or first main body 130 and/or external body, gripping portion, etc. of the first controller 160*a*) may be secured and/or anchored in place (such as via first anchor assembly 120, an anchoring tool (not shown), and/or an operator) relative to the patient (and/or surgical bed).

In an example embodiment, the second controller 160*b* may be operable to control, either through automatic control by a processor and/or manual control by an operator, an actuating (such as a bending, straightening, turning, pivoting, twisting, moving, etc.) of the second main body 150 (such as a bending, straightening, turning, pivoting, twisting, moving, etc. of the first end portion 150*a*) in one or more of a plurality of directions. For example, the second controller 160*b* and/or an element (e.g., 161*b*) associated with the second controller 160*b* (such as a button, joystick, thumbstick, touchpad, motion control, voice control, accelerometer, haptic feedback, or the like, or physical elements such as an external body, gripping portion, etc. of the second controller 160*b*) may be controlled by an operator so as to enable the second main body 150 to actuate as desired by the operator. In this regard, the pressure control subsystem 170, expansion source subsystem 194, and/or the like, associated with or connected to the one or more movement control cavities 153 of the second main body 150, as described above and in the present disclosure, may be controllable by the second controller 160*b* and/or an element (e.g., 161*b*) associated with the second controller 160*b* (such as a button, joystick, thumbstick, touchpad, motion control, voice control, accelerometer, haptic feedback, or the like, or physical elements such as an external body, gripping portion, etc. of the second controller 160*b*) so as to enable the second main body 150 to actuate as desired.

In an example embodiment, the second controller 160*b* may be operable to control, either through automatic control by a processor and/or manual control by an operator, an expanding and/or contracting of the second anchor assembly 140. For example, the second controller 160*b* and/or an element (e.g., 165*b*) associated with the second controller 160*b* (such as a button, joystick, thumbstick, touchpad, motion control, voice control, accelerometer, haptic feedback, or the like, or physical elements such as an external body, gripping portion, etc. of the second controller 160*b*) may be controlled by an operator so as to enable the second anchor assembly 140 to expand and/or contract as desired by the operator. In this regard, expansion source subsystem 194, and/or the like, associated with or connected to the second anchor assembly 140 of the second main body 150, as described above and in the present disclosure, may be controllable by the second controller 160*b* and/or an element (e.g., 165*b*) associated with the second controller 160*b* (such as a button, joystick, thumbstick, touchpad, motion control, voice control, accelerometer, haptic feedback, or the like, or physical elements such as an external body, gripping portion, etc. of the second controller 160*b*) so as to enable the second anchor assembly 140 to expand and/or contract as desired.

In an example embodiment, the second controller 160*b* may be operable to control, either through automatic control by a processor and/or manual control by an operator, an expanding and/or contracting of one or more of the fourth expandable member 142 and third expandable member 144. For example, the second controller 160*b* and/or an element (e.g., 165*b*) associated with the second controller 160*b* (such as a button, joystick, thumbstick, touchpad, motion control, voice control, accelerometer, haptic feedback, or the like, or physical elements such as an external body, gripping portion, etc. of the second controller 160*b*) may be controlled by an operator so as to enable one or more of the fourth expandable member 142 and third expandable member 144 to expand and/or contract as desired by the operator. In this regard, expansion source subsystem 194, and/or the like, associated with or connected to one or more of the fourth expandable member 142 and third expandable member 144, as described above and in the present disclosure, may be controllable by the second controller 160*b* and/or an element (e.g., 165*b*) associated with the second controller 160*b* (such as a button, joystick, thumbstick, touchpad, motion control, voice control, accelerometer, haptic feedback, or the like, or physical elements such as an external body, gripping portion, etc. of the second controller 160*b*) so as to enable one or more of the fourth expandable member 142 and third expandable member 144 to expand and/or contract as desired.

In an example embodiment, the second controller 160*b* may be operable to control, either through automatic control by a processor and/or manual control by an operator, an applying or not applying of a suctioning (or applying negative pressure) via second suction opening(s) 146. For example, the second controller 160*b* and/or an element (e.g., 166*b*) associated with the second controller 160*b* (such as a button, joystick, thumbstick, touchpad, motion control, voice control, accelerometer, haptic feedback, or the like, or physical elements such as an external body, gripping portion, etc. of the second controller 160*b*) may be controlled by an operator so as to enable the second suction opening(s) 146 to apply a suction (or negative pressure) and/or not apply a suction (no pressure or positive pressure) as desired by the operator. In this regard, pressure control subsystem 170, and/or the like, associated with or connected to the second suction opening(s) 146 of the second main body 150, as described above and in the present disclosure, may be controllable by the second controller 160*b* and/or an element (e.g., 166*b*) associated with the second controller 160*b* (such as a button, joystick, thumbstick, touchpad, motion control, voice control, accelerometer, haptic feedback, or the like, or physical elements such as an external body, gripping portion, etc. of the second controller 160*b*) so as to enable the second suction opening(s) 146 to apply and/or not apply suction as desired. It is to be understood in the present disclosure that the second controller 160*b* may be operable to control the expanding and contracting of the second anchor assembly 140 (and/or each of the third and fourth expandable members 144, 142) at the same time as the applying and not applying of the suctioning by the second suction opening(s) 146, respectively (e.g., using a single control, interaction, action, and/or command to perform both). For example, when the second anchor assembly 140 is controlled to expand, the second suction opening(s) 146 may be controlled to apply a suction. Similarly, when the second anchor assembly 140 is controlled to contract, the second suction opening(s) 146 may be controlled to not apply a suction.

In embodiments wherein a second instrument assembly 110' (as illustrated in FIG. 2B) is provided, the second controller 160*b* and/or an element (not shown) associated with the second controller 160*b* (such as a button, joystick, thumbstick, touchpad, motion control, voice control, accelerometer, haptic feedback, or the like, or physical elements such as an external body, gripping portion, etc. of the second controller 160*b*) may be operable to perform one or more actions, operations, configurations, and/or communications with or using the second instrument assembly 110' in a similar or substantially the same manner as described above for the instrument assembly 110. In embodiments wherein a second image capturing assembly (not shown) for capturing images between the first and second anchor assemblies 120 and 140 is provided, the second controller 160*b* and/or an element (not shown) associated with the second controller 160*b* (such as a button, joystick, thumbstick, touchpad, motion control, voice control, accelerometer, haptic feedback, or the like, or physical elements such as an external body, gripping portion, etc. of the second controller 160*b*) may also be operable to perform one or more actions, operations, configurations, and/or communications with or using the second image capturing assembly in a similar or substantially the same manner as described above for the image capturing assembly 111. In embodiments wherein a second irrigation cavity (not shown) for enabling movement of solids and/or liquids between the area between the first and second anchor assemblies 120 and 140 is provided, the second controller 160*b* and/or an element (not shown) associated with the second controller 160*b* (such as a button, joystick, thumbstick, touchpad, motion control, voice control, accelerometer, haptic feedback, or the like, or physical elements such as an external body, gripping portion, etc. of the second controller 160*b*) may also be operable to perform one or more actions, operations, configurations, and/or communications with or using the second irrigation cavity in a similar or substantially the same manner as described above for the irrigation cavity 134. In embodiments wherein a second insufflation cavity (not shown) for providing insufflation to the area between the first and second anchor assemblies 120 and 140 is provided, the second controller 160*b* and/or an element (not shown) associated with the second controller 160*b* (such as a button, joystick, thumbstick, touchpad, motion control, voice control, accelerometer, haptic feedback, or the like, or physical elements such as an external body, gripping portion, etc. of the second controller 160*b*) may be operable to perform one or more actions, operations, configurations, and/or communications with or using the second insufflation cavity in a similar or substantially the same manner as described above for the insufflation cavity 135.

Method of Configuring the Endoscopic Device (e.g., Method 500)

Figure 5:
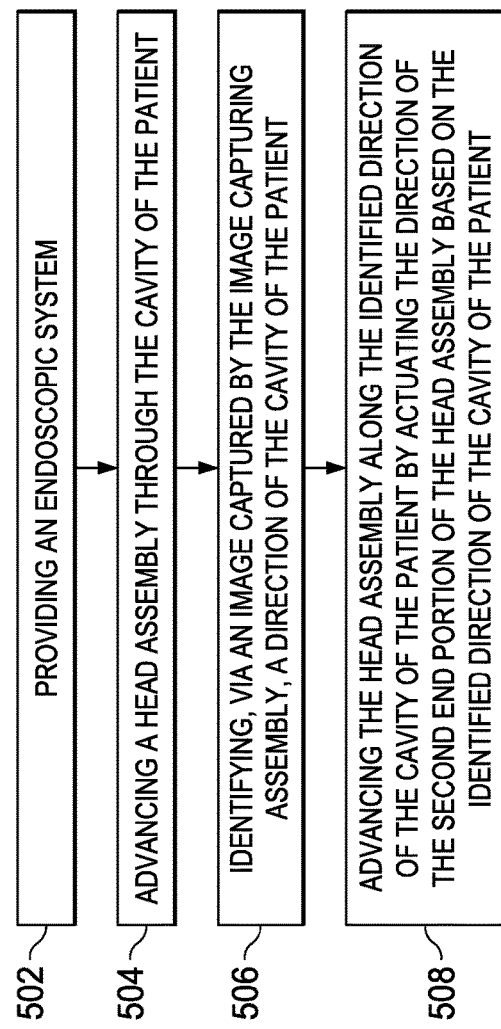
FIG. 5 is an illustration of an example embodiment of a method for performing a diagnostic and/or therapeutic/surgical action and/or procedure in a cavity of a patient.

Example embodiments of the endoscopic device 100 may be configurable to perform diagnostic and/or therapeutic/surgical actions and/or procedures in one of a plurality of ways. In an example embodiment, as illustrated in FIG. 5, a method 500 of performing and/or configuring a endoscopic system 100 to perform a diagnostic and/or therapeutic/surgical action and/or procedure in a cavity of a patient may comprise one or more of the actions described below. The one or more actions may be performed using an example embodiment of controller 160, first controller 160*a*, and/or second controller 160*b*.

In an example embodiment, the method 500 may comprise providing an endoscopic system (e.g., action 502). The endoscopic device provided may include one or more elements of the endoscopic device 100 described above and in the present disclosure. In an example embodiment, the provided endoscopic device may comprise a first main body. The first main body may be an elongated body having a first end. The provided endoscopic device may further comprise a second main body. The second main body may have a first end and a main cavity. The main cavity may house at least a portion of the first main body. The first main body and second main body may be slidable with respect to each other. The provided endoscopic device may further comprise an anchor assembly attached to the first main body near the first end of the first main body. The anchor assembly may comprise a first expandable member. The first expandable member may be configurable to expand radially away from the first main body. The anchor assembly may further comprise a second expandable member provided between the first expandable member and the first end of the first main body. The second expandable member may be configurable to expand radially away from the first main body. The provided endoscopic device may further comprise a second anchor assembly attached to the second main body near the first end of the second main body. The second anchor assembly may comprise a third expandable member. The third expandable member may be configurable to expand radially away from the second main body. The second anchor assembly may further comprise a fourth expandable member provided between the third expandable member and the first end of the second main body. The fourth expandable member may be configurable to expand radially away from the second main body. The provided endoscopic device may further comprise a head assembly. The head assembly may comprise a first end portion and a second end portion opposite to the first end portion. The first end portion may be attachable to the first end of the first main body. The second end portion may be selectively configurable to actuate in a plurality of directions with respect to the first end portion. The head assembly may further comprise an image capturing assembly provided in the second end portion. The image capturing assembly may be configurable to capture an image. The head assembly may further comprise an instrument section provided in the second end portion. The instrument section may be configurable to provide an instrument. The instrument may comprise at least two degrees of freedom of movement for performing an in vivo procedure in the cavity of the patient. The endoscopic system may further comprise a controller.

The method 500 may further comprise advancing a head assembly of the endoscopic system through the cavity of the patient (e.g., action 504). In this regard, the first end portion of the head assembly may be fixedly attached to the first end of the first main body. Furthermore, at least a portion of the first main body may be housed in the main cavity of the second main body. The head assembly may be advanced via the controller, such as the first controller described above and in the present disclosure.

The method 500 may further comprise identifying, via an image captured by an image capturing assembly of the endoscopic system, a direction of the cavity of the patient (e.g., action 506). For example, as illustrated in FIG. 3D, the image captured by the image capturing assembly may identify that an upcoming section or region of the cavity of the patient includes a bend. The identifying, via the image capturing assembly, of the direction of the cavity of the patient may be performed via the controller, such as the first controller described above and in the present disclosure.

The method 500 may further comprise advancing the head assembly along the identified direction of the cavity of the patient (e.g., action 508). For example, the head assembly may continue to move forward in a straight or relatively straight region of the cavity of the patient. The head assembly may be advanced via the controller, such as the first controller described above and in the present disclosure.

The method 500 may further comprise, when a bend section (such as a flexural and/or looping/bending section of a colon) in the cavity of the patient is identified, actuating, at the bend section in the cavity of the patient, the direction of a second end portion of the head assembly based on the identified direction of the bend section in the cavity of the patient (e.g., action 510). For example, as illustrated in FIG. 3D, when a bend in the cavity of the patient is identified (e.g., action 506), the second end portion (i.e., tip) of the head assembly may be actuated to move forward (and/or extend outwardly) and also bend based on the identified direction of the bend section in the cavity of the patient. The actuating the direction of the second end portion of the head assembly may be performed via the controller, such as the first controller described above and in the present disclosure.

The method 500 may further comprise, when a bend section in the cavity, such as a colonic lumen, of the patient is identified, advancing the head assembly through the bend section (e.g., action 512). The head assembly may be advanced through the bend section via the controller, such as the first controller described above and in the present disclosure.

The method 500 may further comprise, when a bend section in the cavity of the patient is identified, actuating, after advancing through the bend section, the direction of the second end portion of the head assembly based on a direction of the cavity of the patient identified after the bend section (e.g., action 514). For example, as illustrated in FIG. 3E, after passing through the bend section of the cavity of the patient, the second end portion of the head assembly may be straightened (or adjusted) based on the direction of the cavity after the bend section (which can be identified based on another image captured by the image capturing assembly). The actuating the direction of the second end portion of the head assembly may be performed via the controller, such as the first controller described above and in the present disclosure.

The method 500 may further comprise, prior to the actuating, at the bend section, of the direction of the second end portion of the head assembly, securing the second main body to an interior wall forming the cavity of the patient by expanding the third expandable member to contact the interior wall forming the cavity of the patient, and expanding the fourth expandable member to contact the interior wall forming the cavity of the patient (e.g., action 516). For example, as illustrated in FIG. 3D, the second main body may be secured to the interior wall forming the cavity of the patient by expanding the second anchor assembly to secure or anchor to the interior wall forming the cavity of the patient. The securing of the second main body may also be provided using the second suction opening (i.e., applying a negative pressure) and/or the surface pattern, roughness, and/or protrusion (if provided) of the surface of the third and fourth expansion members of the second anchor assembly. The securing the second main body to the interior wall forming the cavity of the patient via expanding the third expandable member and fourth expandable member may be performed via the controller, such as the second controller described above and in the present disclosure.

The method 500 may further comprise securing the first main body to an interior wall forming the cavity of the patient by expanding the first expandable member to contact the interior wall forming the cavity of the patient and expanding the second expandable member to contact the interior wall forming the cavity of the patient (e.g., action 518). For example, as illustrated in FIG. 3D, the main body may be secured to the interior wall forming the cavity of the patient by expanding the anchor assembly to secure or anchor to the interior wall forming the cavity of the patient. The securing of the main body may also be provided using the suction opening (i.e., applying a negative pressure) and/or the surface pattern, roughness, and/or protrusion (if provided) of the surface of the first and second expansion members of the anchor assembly. After the head assembly is advanced through the bend section, the first main body may be unsecured or unanchored from the interior wall forming the cavity of the patient. This may be achieved by unexpanding (or contracting) the first and second expandable members of the first anchor assembly, and may also include not applying a negative pressure by the suction opening. Thereafter, the first main body may also be advanced through the bend section by actuating the direction of the first main body based on the direction of the bend in the cavity of the patient. The securing the first main body to the interior wall forming the cavity of the patient via expanding the first expandable member and second expandable member may be performed via the controller, such as the first controller described above and in the present disclosure.

The method 500 may further comprise advancing the second main body through the bend section towards the head assembly, the advancing of the second main body operable to reduce the bending of the bend section in the cavity of the patient (e.g., action 520). Before doing so, as illustrated in FIG. 3F, the main body may be secured to the interior wall (after the bend) forming the cavity of the patient by expanding the anchor assembly to secure or anchor to the interior wall forming the cavity of the patient. The securing of the main body may also be provided using the suction opening (i.e., applying a negative pressure) and/or the surface pattern, roughness, and/or protrusion (if provided) of the surface of the first and second expansion members of the anchor assembly. Thereafter, the second main body may be unsecured or unanchored from the interior wall forming the cavity of the patient. This may be achieved by un-expanding (or contracting) the third and fourth expandable members of the second anchor assembly, and may also include not applying a negative pressure by the second suction opening. Once completed, the second main body may also be advanced through the bend section by actuating the direction of the second main body based on the direction of the bend in the cavity of the patient, as illustrated in FIG. 3F. The advancing of the second main body may be performed via the controller, such as the second controller described above and in the present disclosure. The securing and unsecuring of the main body to the interior wall may be performed via the controller, such as the first controller described above and in the present disclosure.

In example embodiments, the identified bend section in the cavity of the patient may be straightened (or made less looping/bending) by actuating the direction of the second main body, as illustrated in FIG. 3G. It is recognized in the present disclosure that such straightening of a bend section in the cavity of the patient may enable easier, quicker, and/or more efficient advancing of the endoscopic system into the remaining sections of the cavity of the patient. Furthermore, it is recognized in the present disclosure that such straightening of the bend section in the cavity, such as the colonic lumen, of the patient also enables easier, quicker, and/or more efficient removal, extraction, and/or retracting of the endoscopic system from the cavity of the patient after completing the diagnostic and/or therapeutic/surgical procedure. The actuating of the direction of the second main body to straighten the identified bend section in the cavity of the patient may be performed via the controller, such as the second controller described above and in the present disclosure.

The method 500 may further comprise identifying, via the image captured by the image capturing assembly, a location in the cavity of the patient for the instrument to perform the procedure (e.g., action 522). The identifying, via the image capturing assembly, of the location in the cavity of the patient for the instrument to perform the procedure may be performed via the controller, such as the first controller described above and in the present disclosure.

The method 500 may further comprise securing the first main body to an interior wall forming the cavity of the patient by expanding the first expandable member to contact the interior wall forming the cavity of the patient and expanding the second expandable member to contact the interior wall forming the cavity of the patient (e.g., action 524), as illustrated in FIG. 2C. In this regard, the third expandable member and/or the fourth expandable member may also be expanded to contact the interior wall forming the cavity of the patient. The securing of the first main body to the interior wall forming the cavity of the patient via expanding the first expandable member may be performed via the controller, such as the first controller described above and in the present disclosure.

The method 500 may further comprise actuating the instrument to perform the procedure based on the image captured by the image capturing assembly (e.g., action 526), as illustrated in FIG. 2C. The actuating of the instrument may be performed via the controller, such as the first controller described above and in the present disclosure.

It is to be understood in the present disclosure that one or more of the aforementioned actions of method 500 may be performed manually, either in whole or in part, by an operator/surgeon and/or assisted by the controller 160 in example embodiments.

While various embodiments in accordance with the disclosed principles have been described above, it should be understood that they have been presented by way of example only, and are not limiting. Thus, the breadth and scope of the example embodiments described in the present disclosure should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

For example, "assembly," "device," "portion," "segment," "member," "body," or other similar terms should generally be construed broadly to include one part or more than one part attached or connected together.

Various terms used herein have special meanings within the present technical field. Whether a particular term should be construed as such a "term of art" depends on the context in which that term is used. "Connected," "connecting," "attached," "attaching," "anchored," "anchoring," "in communication with," "communicating with," "associated with," "associating with," or other similar terms should generally be construed broadly to include situations where attachments, connections, and anchoring are direct between referenced elements or through one or more intermediaries between the referenced elements. These and other terms are to be construed in light of the context in which they are used in the present disclosure and as one of ordinary skill in the art would understand those terms in the disclosed context. The above definitions are not exclusive of other meanings that might be imparted to those terms based on the disclosed context.

As referred to in the present disclosure, a computing device, a processor, and/or a system may be a virtual machine, computer, node, instance, host, and/or device in a networked or non-networked computing environment. A networked computing environment may be a collection of devices connected by communication channels that facilitate communications between devices and allow devices to share resources. Also as referred to in the present disclosure, a computing device may be a device deployed to execute a program operating as a socket listener and may include software instances.

Resources may encompass any type of resource for running instances including hardware (such as servers, clients, mainframe computers, networks, network storage, data sources, memory, central processing unit time, scientific instruments, and other computing devices), as well as software, software licenses, available network services, and other non-hardware resources, or a combination thereof.

A networked computing environment may include, but is not limited to, computing grid systems, distributed computing environments, cloud computing environment, etc. Such networked computing environments include hardware and software infrastructures configured to form a virtual organization comprised of multiple resources that may be in geographically disperse locations.

Furthermore, the coverage of the present application and any patents issuing from the present application may extend to one or more communications protocols, including TCP/IP.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention (s), and their equivalents, that are protected thereby. In all instances, the scope of such claims shall be considered on their own merits in light of this disclosure, but should not be constrained by the headings herein.

What is claimed is:

1. An endoscopic system configurable to be provided in a cavity of a patient, the endoscopic system comprising:
    a first main body, the first main body being an elongated body, the first main body including:
        a first end, the first end of the first main body located at a distal end of the first main body, the first end of the first main body controllable to bend in a plurality of directions;
        a first anchor assembly at the first end of the first main body, the first anchor assembly including:
            a first expandable member secured to the first main body, the first expandable member configurable to expand radially away from the first main body;
            a second expandable member secured to the first main body, the second expandable member configurable to expand radially away from the first main body; and
            a first negative pressure opening provided on the first main body between the first expandable member and the second expandable member, the first negative pressure opening configurable to apply a negative pressure;
            wherein the first expandable member, the second expandable member, and the first negative pressure opening are configured to cooperate to sufficiently anchor the first main body to an interior wall forming a colonic lumen so as to withstand a force of at least 0.1 N when the first and second expandable members are expanded radially away from the first main body and the first negative pressure opening applies a negative pressure;
    a second main body, the second main body being an elongated body having a main cavity, the main cavity housing at least a portion of the first main body and not housing at least a portion of the first end of the first main body, the second main body including:
        a first end, the first end of the second main body located at a distal end of the second main body, the first end of the second main body controllable to bend in a plurality of directions, wherein the bending of the first end of the second main body is controllable independently from the bending of the first end of the first main body;
        a second anchor assembly at the first end of the second main body, the second anchor assembly including:
            a third expandable member secured to the second main body, the third expandable member configurable to expand radially away from the second main body; and
            a second negative pressure opening provided on the second main body, the second negative pressure opening configurable to apply a negative pressure, wherein the third expandable member is positioned between the second negative pressure opening and a most distal portion of the first end of the second main body; and
    a head assembly, the head assembly being an elongated body, the head assembly including:
        a first end portion and second end portion opposite to the first end portion of the head assembly, at least a portion of the first end portion of the head assembly housed within and adjacent the first end of the first main body, wherein a length of the head assembly is between about 10-100 mm. wherein at least a portion of the head assembly that extends outwardly away from the first end of the first main body is configurable to bend in a plurality of directions, wherein the bending of the portion of the head assembly that extends outwardly away from the first end of the first main body is controllable independently from the bending of the first end of the first main body; and
        a suction/irrigation opening provided at the most distal portion of the second end portion of the head assembly, the suction/irrigation opening configurable to enable an exchange of fluids and/or solids between an exterior of the most distal portion of the second end portion of the head assembly and the endoscopic system;
    wherein the first main body and second main body are configurable to slide relative to one another in such a way that a length of the first main body that extends outwardly away from the first end of the second main body is adjustable; and
    wherein the head assembly and first main assembly are configurable to slide relative to one another in such a way that a length of the head assembly that extends outwardly away from the first end of the first main body is adjustable.

2. The endoscopic system of claim 1, further comprising a pressure control subsystem configurable to provide the negative pressure through the first negative pressure opening.

3. The endoscopic system of claim 1, wherein the expanding of the first expandable member corresponds with the negative pressure applied through the first negative pressure opening.

4. The endoscopic system of claim 1, wherein an exterior surface of one or more of the first and second expandable members include a surface pattern, roughness, and/or protrusion, the surface pattern, roughness, and/or protrusion; configured to resist a movement of one or more of the first and second expandable members with respect to the interior wall forming the cavity of the patient when one or more of the first and second expandable members are in contact with.

5. The endoscopic system of claim 1, wherein the head assembly further comprises a plurality of movement control cavities, each movement control cavity configurable to receive a filler; and
wherein the second end portion is actuated in the plurality of directions by selectively controlling the filler in one or more of the plurality of movement control cavities.

6. The endoscopic system of claim 1, wherein the head assembly further comprises an image capturing assembly, the image capturing assembly configurable to capture an image.

7. The endoscopic system of claim 1, wherein the head assembly is configurable to provide an instrument at the second end portion of the head assembly, the instrument for use in performing an in vivo procedure in the cavity of the patient.

8. The endoscopic system of claim 1, wherein the first main body further comprises a plurality of cavities, including a first cavity and a second cavity, the first cavity operable to provide a filler to expand the first expandable member, and the second cavity in communication with the pressure control subsystem and the first negative pressure opening.

9. The endoscopic system of claim 1, wherein:
the second anchor assembly further includes:
a fourth expandable member secured to the second main body and provided in such a way that the second negative pressure opening is provided between the third expandable member and the fourth expandable member, the fourth expandable member configurable to expand radially away from the second main body.

10. The endoscopic system of claim 1, further comprising a pressure control subsystem configurable to provide the negative pressure through the second negative pressure opening.

11. The endoscopic system of claim 9, wherein an exterior surface of one or more of the third and fourth expandable members include a surface pattern, roughness, and/or protrusion, the surface pattern, roughness, and/or protrusion configured to resist a movement of one or more of the third and fourth expandable members with respect to the interior wall forming the cavity of the patient when one or more of the third and fourth expandable members are in contact with the interior wall forming the cavity of the patient.

12. The endoscopic system of claim 6, further comprising a controller in communication with the head assembly, the controller operable to control the image capturing assembly, the controller further operable to actuate the direction of the second end portion of the head assembly.

13. The endoscopic system of claim 12, wherein the actuating the direction of the second end portion of the head assembly is based on the image captured by the image capturing assembly and/or a sensor provided at the second end portion of the head assembly.

14. The endoscopic system of claim 12, wherein the controller is further operable to control the instrument provided at the second end portion of the head assembly to perform the in vivo procedure in the cavity of the patient.

15. The endoscopic system of claim 14, wherein the controlling of the instrument to perform the in vivo procedure in the cavity of the patient is based on the image captured by the image capturing assembly and/or the sensor provided at the second end portion of the head assembly.

16. The endoscopic system of claim 1, further comprising a controller in communication with the anchor assembly, the controller operable to control the expanding of the first expandable member and the second expandable member.

17. The endoscopic system of claim 1, wherein at least a portion of the head assembly is fixedly secured to the first end of the first main body.

18. The endoscopic system of claim 1, wherein the first negative pressure opening is configurable to apply a negative pressure of a magnitude of at least 10 kPa.

19. An endoscopic system, the endoscopic system comprising:
a first main body, the first main body being an elongated body, the first main body including:
a first end, the first end of the first main body located at a distal end of the first main body;
a plurality of movement control cavities for the first main body, including a first movement control cavity and a second movement control cavity, the first movement control cavity controllable so as to cause the first end of the first main body to bend in a first direction, the second movement control cavity controllable so as to cause the first end of the first main body to bend in a second direction different from the first direction;
a first anchor assembly at the first end of the first main body, the first anchor assembly including:
a first expandable member secured to the first main body, the first expandable member configurable to expand radially away from the first main body;
a second expandable member secured to the first main body, the second expandable member configurable to expand radially away from the first main body; and
a first negative pressure opening provided on the first main body between the first expandable member and the second expandable member, the first negative pressure opening configurable to apply a negative pressure; and
wherein the first expandable member, the second expandable member, and the first negative pressure opening are configured to cooperate to sufficiently anchor the first main body to an interior wall forming a colonic lumen so as to withstand a force of at least 0.1 N when the first and second expandable members are expanded radially away from the first main body and the first negative pressure opening applies a negative pressure;
a second main body, the second main body being an elongated body having a main cavity, the main cavity housing at least a portion of the first main body and not housing at least a portion of the first end of the first main body, the second main body including:
a first end, the first end of the second main body located at a distal end of the second main body;
a plurality of movement control cavities for the second main body, including a third movement control cavity and a fourth movement control cavity, the third movement control cavity controllable so as to cause the first end of the second main body to bend in a third direction, the fourth movement control cavity controllable so as to cause the first end of the second main body to bend in a fourth direction different from the third direction, wherein the bending of the first end of the second main body is controllable independently from the bending of the first end of the first main body;
a second anchor assembly at the first end of the second main body, the second anchor assembly including:

a third expandable member secured to the second main body, the third expandable member configurable to expand radially away from the second main body; and
a second negative pressure opening provided on the second main body, the second negative pressure opening configurable to apply a negative pressure, wherein the third expandable member is positioned between the second negative pressure opening and a most distal portion of the first end of the second main body; and
a head assembly, the head assembly including:
a first end portion and second end portion opposite to the first end portion of the head assembly, at least a portion of the first end portion of the head assembly housed within and adjacent the first end of the first main body, wherein a length of the head assembly is between about 10-100 mm. wherein the head assembly is configurable to bend in a plurality of directions, wherein the bending of the portion of the head assembly is controllable independently from the bending of the first end of the first main body.

20. The endoscopic system of claim 19, further comprising a pressure control subsystem configurable to provide the negative pressure through the first negative pressure opening.

21. The endoscopic system of claim 19, wherein the expanding of the first expandable member corresponds with the negative pressure applied through the first negative pressure opening.

22. The endoscopic system of claim 19, wherein the head assembly further comprises an image capturing assembly, the image capturing assembly configurable to capture an image.

23. The endoscopic system of claim 19, wherein the head assembly is configurable to provide an instrument at the second end portion of the head assembly, the instrument for use in performing an in vivo procedure in the cavity of the patient.

24. The endoscopic system of claim 19, wherein:
the second anchor assembly further includes:
a fourth expandable member secured to the second main body and provided in such a way that the second negative pressure opening is provided between the third expandable member and the fourth expandable member, the fourth expandable member configurable to expand radially away from the second main body.

25. The endoscopic system of claim 19, further comprising a pressure control subsystem configurable to provide the negative pressure through the second negative pressure opening.

26. An endoscopic system, the endoscopic system comprising:
a first main body, the first main body being an elongated body, the first main body including:
a first end, the first end of the first main body located at a distal end of the first main body;
a plurality of movement control cavities for the first main body, including a first movement control cavity and a second movement control cavity, the first movement control cavity controllable so as to cause the first end of the first main body to bend in a first direction, the second movement control cavity controllable so as to cause the first end of the first main body to bend in a second direction different from the first direction;
a first anchor assembly at the first end of the first main body, the first anchor assembly including:
a first expandable member secured to the first main body, the first expandable member configurable to expand radially away from the first main body;
a second expandable member secured to the first main body, the second expandable member configurable to expand radially away from the first main body; and
a first negative pressure opening provided on the first main body between the first expandable member and the second expandable member, the first negative pressure opening configurable to apply a negative pressure;
wherein the first expandable member, the second expandable member, and the first negative pressure opening are configured to cooperate to sufficiently anchor the first main body to an interior wall forming a colonic lumen so as to withstand a force of at least 0.1 N when the first and second expandable members are expanded radially away from the first main body and the first negative pressure opening applies a negative pressure;
a second main body, the second main body being an elongated body having a main cavity, the main cavity housing at least a portion of the first main body and not housing at least a portion of the first end of the first main body, the second main body including:
a first end, the first end of the second main body located at a distal end of the second main body, wherein at least a portion of the first end of the second main body is controllable to bend in a plurality of directions, wherein the bending of the first end of the second main body is controllable independently from the bending of the first end of the first main body; and
a second anchor assembly at the first end of the second main body, the second anchor assembly including:
a second third expandable member secured to the second main body, the second third expandable member configurable to expand radially away from the second main body; and
a second negative pressure opening provided on the second main body, the second negative pressure opening configurable to apply a negative pressure, wherein the second third expandable member is positioned between the second negative pressure opening and a most distal portion of the first end of the second main body; and
a head assembly, the head assembly being an elongated body, the head assembly including:
a first end, the first end of the head assembly located at a distal end of the head assembly, at least a portion of the first end of the head assembly housed within and adjacent the first end of the first main body, wherein at least a portion of the first end of the head assembly is controllable to bend in a plurality of directions, wherein a length of the head assembly is between about 10-100 mm.

27. The endoscopic system of claim 26, further comprising a pressure control subsystem configurable to provide the negative pressure through the first negative pressure opening.

28. The endoscopic system of claim 26, wherein the expanding of the first expandable member corresponds with the negative pressure applied through the first negative pressure opening.

29. The endoscopic system of claim 26, wherein the head assembly further comprises an image capturing assembly, the image capturing assembly configurable to capture an image.

30. The endoscopic system of claim 26, wherein the head assembly is configurable to provide an instrument at the second end portion of the head assembly, the instrument for use in performing an in vivo procedure in the cavity of the patient.

31. The endoscopic system of claim 26, wherein:
the second anchor assembly further includes:
- a fourth expandable member secured to the second main body and provided in such a way that the second negative pressure opening is provided between the third expandable member and the fourth expandable member, the fourth expandable member configurable to expand radially away from the second main body.

32. The endoscopic system of claim 26, further comprising a pressure control subsystem configurable to provide the negative pressure through the second negative pressure opening.

* * * * *